(12) United States Patent
Ellington et al.

(10) Patent No.: US 6,593,309 B2
(45) Date of Patent: *Jul. 15, 2003

(54) METHODS AND COMPOSITIONS TO IMPROVE GERM CELL AND EMBRYO SURVIVAL AND FUNCTION

(75) Inventors: Joanna E. Ellington, Valleyford, WA (US); Sylvia Adams Oliver, Spokane, WA (US)

(73) Assignee: Bio-Origyn LLC, Spokane, WA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/514,412

(22) Filed: Feb. 28, 2000

(65) Prior Publication Data

US 2002/0193350 A1 Dec. 19, 2002

Related U.S. Application Data

(63) Continuation of application No. 08/733,227, filed on Oct. 17, 1996, now Pat. No. 6,140,121.
(60) Provisional application No. 60/007,081, filed on Oct. 19, 1995.

(51) Int. Cl.$^7$ .................. A61K 31/715; A61K 49/00; A01N 1/02
(52) U.S. Cl. .................. 514/54; 435/2; 424/9.1
(58) Field of Search .................. 424/725, 9.1; 514/54; 435/2

(56) References Cited

U.S. PATENT DOCUMENTS

| 3,393,678 | A | * | 7/1968 | Picini .................. 128/270 |
| 3,718,740 | A | | 2/1973 | Hafs et al. .................. 424/105 |
| 4,007,087 | A | | 2/1977 | Ericsson .................. 195/1.8 |
| 4,039,662 | A | | 8/1977 | Hecht et al. .................. 424/180 |
| 4,804,537 | A | | 2/1989 | Bergman et al. .................. 424/105 |
| 4,804,674 | A | * | 2/1989 | Curtis-Prior et al. .................. 514/400 |
| 4,818,751 | A | | 4/1989 | Ibe .................. 514/54 |
| 5,071,741 | A | | 12/1991 | Brockbank .................. 435/1 |
| 5,116,969 | A | | 5/1992 | Adams et al. .................. 536/128 |
| 5,198,217 | A | * | 3/1993 | Vedros .................. 424/195.1 |

FOREIGN PATENT DOCUMENTS

| DE | 35 16398 | * | 11/1985 |
| EP | 380 084 A2 | | 8/1990 |
| EP | 0 608 511 | * | 8/1994 |
| EP | 661 028 A1 | | 7/1995 |
| JP | 59059605 | * | 4/1984 |
| JP | 5-076332 | | 3/1993 |
| SU | 604556 | | 4/1978 |
| SU | 685285 | | 9/1979 |

OTHER PUBLICATIONS

The Merck Index. Encyclopedia of Chemicals, Drugs and Biologicals. 1989, pp. 284, 285, 705, 1118, 1139.*

Bongso et al., "Improved sperm concentration, motility, and fertilization rates following Ficoll treatment of sperm in a human in vitro fertilization program," *Fertility and Sterility* 51(5):850–854, 1989.

Buchala et al., "Polysaccharides in the culture medium of cotton cells cultured in vitro," *Food Hydrocolloids* 1(5/6):359–363, 1987.

G. Maisse, "Comparison of different carbohydrates for the cryopreservation of rainbow trou (*Oncorhynchus mykiss*) sperm," *CAB International*, Abstract No. 940104586, 1994 & see also *Aquatic Living Resources* 7(3):217–219, 1994.

Garcia et al., "Development of a buffer system for dialysis of . . . ," *Theriogenology* 31(5), Abstract only, 1989.

Hill et al., "Use of arabinogalactan to obtain washed murine platelets free of contaminating plasma proteins and appropriate for studies of function, morphology, and thrombopoiesis," *The Journal of Laboratory and Clinical Medicine, 61$^{st}$ Annual Meeting*, Nov. 9–11, 1988.

Karow et al., "Effects of Temperature, Potassium Concentration, and Sugar on Human Spermatozoa Motility: A Cell Preservation Model from Reproductive Medicine," *Cryobiology* 29:250–254, 1992.

Katsoff et al., "Chymotrypsin–galactose treatment of sperm with antisperm antibodies result in improved pregnancy rates following in vitro fertilization," *American Journal of Reproductive Immunology* 33:149–154, 1995.

Neuwinger et al., "Hyaluronic acid as a medium for human sperm migration tests," *Human Reproduction* 6(3):396–400, 1991.

Platov et al., "Freezing ram semen in diluents containing polysaccharides," *CAB International* Abstract No. 810160548, 1980.

Amelar et al., "Sperm Motility," *Fertility and Sterility* 34(3):197–215, Sep. 1980.

Boyers et al., "The Effects of Lubrin on Sperm Motility In Vitro," *Fertility and Sterility* 47(5):882–884, May 1987.

(List continued on next page.)

*Primary Examiner*—Sandra E. Saucier
*Assistant Examiner*—Vera Afremova
(74) *Attorney, Agent, or Firm*—Seed Intellectual Property Law Group PLLC

(57) ABSTRACT

Sperm, oocyte, and embryo survival and function is improved in vivo or in vitro by the use of a polysaccharide containing arabinose, galactose and/or hexuronic acid. In particular, a nonspermicidal lubricant containing such a polysaccharide (e.g., gum arabic, pectin, or galacturonic acid) increases the fertilization potential of the sperm during coitus, artificial insemination or sperm collection. Similarly, a freezing medium containing a polysaccharide containing arabinose, galactose and/or hexuronic acid enhances sperm, oocyte, or embryo viability.

6 Claims, 19 Drawing Sheets

OTHER PUBLICATIONS

Frishman et al., "Evaluation of Astroglide, a New Vaginal Lubricant: Effects of Length of Exposure and Concentration on Sperm Motility," *Fertility and Sterility* 58(3):630–632, Sep. 1992.

Goldenberg and White, "The Effect of Vaginal Lubricants in Sperm Motility In Vitro," *Fertility and Sterility* 26(9):872–873, Sep. 1975.

Kutteh et al., "Vaginal Lubricants for the Infertile Couple: Effect on Sperm Activity," *Int. J. Fertil.* 41(4):400–404, 1996.

Miller et al., "The Effect of a Surgical Lubricant on In Vivo Sperm Penetration of Cervical Mucus," *Fertility and Sterility* 61(6):1171–1173, Jun. 1994.

Tagatz et al., "The Effect of Vaginal Lubricants on Sperm Motility and Viability In Vitro," *Am. J. Obstet. Gynecol.* 113(1):88–90, 1972.

Tulandi and McInnes, "Vaginal Lubricants: Effect of Glycerin and Egg White on Sperm Motility and Progression In Vitro," *Fertility and Sterility* 41(1):151–153, Jan. 1984.

* cited by examiner

Lane 2 Pectin uncut
Lane 3 Pectin cut with EndoA
Lane 4 Pectin cut with AF
Lane 5 Pectin cut with EndoPG
Lane 6 Pectin cut with all three enzymes together
Lane 7 Same as lane 6 but with twice as much loaded A: Control TALP
B: 0.05% Pectin in TALP
C: Pectin Fraction <100Kd
D: Pectin Fraction >100Kd, <0.2u
E: Pectin Fraction >0.2u ions involve
METHODS AND COMPOSITIONS TO IMPROVE GERM CELL AND EMBRYO SURVIVAL AND FUNCTION

CROSS-REFERENCE TO RELATED APPLICATION

This application is a continuation of U.S. patent application Ser. No. 08/733,227, filed Oct. 17, 1996, which issued as U.S. Pat. No. 6,140,121; which application claims the benefit of U.S. Provisional Application No. 60/007,081, filed Oct. 19, 1995 and abandoned.

TECHNICAL FIELD

The present invention relates generally to the use of polysaccharides containing arabinose, galactose and/or hexuronic acid in promoting in vivo and in vitro survival and improved function of sperm, oocytes, and embryos.

BACKGROUND OF THE INVENTION

In nature, fertilization occurs by sperm cells being deposited into the female of warm-blooded animal species (including humans) and then binding to and fusing with an oocyte. This fertilized oocyte then divides to form an embryo. Over the last several decades, the use of assisted reproduction techniques has allowed scientists and clinicians to intervene in these events to treat poor fertility in some individuals or to store sperm, oocytes or embryos for use at other locations or times. The procedures utilized in these cases include: washing a sperm sample to separate out the sperm-rich fraction from non-sperm components of a sample such as seminal plasma or debris; further isolating the healthy, motile (swimming) sperm from dead sperm or from white blood cells in an ejaculate; freezing or refrigerating of sperm (storage) for use at a later date or for shipping to females at differing locations; extending or diluting sperm for culture in diagnostic testing or for use in therapeutic interventions such as in vitro fertilization (IVF) or intracytoplasmic sperm injection (ICSI); culturing or freezing oocytes from the female for use in in vitro fertilization; and culturing or freezing of embryos prior to transfer back to a female in order to establish a pregnancy.

At each step of the way, in vitro intervention decreases the normal survival and function of sperm, oocytes, and embryos. Much research has been dedicated towards improving these procedures; however, overall success remains limited. For example, <20% of IVF attempts result in the birth of a child. Additionally, only half or less of sperm cells routinely survive the freezing process, such that pregnancy rates with frozen sperm from donors average between 10 and 20%. Oocytes and embryos also show significantly disrupted function after culture or freezing. Specifically, human oocytes survive the freezing process at very low levels. Thus, in spite of several decades of work, much room remains for improvement in the field of assisted reproduction technologies and especially in gamete and embryo handling, culture, and storage.

One common procedure used in sperm collection is washing sperm cells. Washing sperm prior to its use in assisted reproduction technologies is important for a variety of reasons. An ejaculate contains seminal plasma in addition to sperm cells, and the sugars and proteins in seminal plasma can be toxic to sperm cells after ejaculation. Also, sperm samples that have been frozen contain cryopreservation media which needs to be washed from the sperm cells prior to insemination in the female of some species, particularly birds and women. For all species, cryopreservative media cause lipid membrane peroxidation (LPO) and degeneration of the sperm after thawing. Generally, washing involves centrifuging a sample of semen or thawed sperm through a diluting wash media, which allows collection of a sperm-rich pellet. Although a very common procedure, centrifugation itself can cause sperm lipid peroxidation and membrane breakdown.

After a sperm wash process, or in place of it, a specific procedure for the isolation of the motile sperm from a sample may be done. An ejaculate contains dead and dying sperm that release enzymes that can damage the live, motile sperm. In addition, an ejaculate contains white blood cells, red blood cells, and bacteria which are also toxic to the healthy sperm in an ejaculate. Sperm isolations involve separating out the live, healthy, and motile sperm for use in diagnostic or therapeutic procedures. Generally, sperm are isolated by allowing the motile sperm to swim away from the dead sperm and debris (sperm swim-up), by centrifuging the sperm through a density gradient, or by passing the sperm through a column that binds the dead sperm and debris. Each of these techniques has its own disadvantages. Swim-up only recovers low sperm numbers, and it requires a long culture period. Current centrifugation gradient reagents are generally toxic to sperm, such that an added wash step is necessary to remove the gradient solution from the sperm sample. Column methods have poor selectivity for motile sperm and do not always result in good recovery of sperm numbers from a full ejaculate.

Once sperm have been washed or isolated, they are then extended (or diluted) in culture or holding media for a variety of uses. Existing sperm culture techniques result in losses of motile sperm and also damage sperm DNA over time in culture. Although sperm survive for days in the females of most species, sperm survival in culture is typically only half as long as that seen in vivo, and sperm from males with poor quality ejaculates may survive for even shorter time periods in culture. Much of this damage is due to lipid peroxidation of the membrane and DNA or chromatin breakdown. Sperm are extended in media for use in sperm analysis and diagnostic tests; assisted reproduction technologies, such as IVF, gamete intrafallopian transfer, or ICSI; insemination into the female; and holding prior to cryopreservation. Each of these uses for extended or diluted sperm requires a somewhat different formulation of basal medium; however, in all cases sperm survival is suboptimal outside of the female reproductive tract.

Likewise, oocytes and embryos often develop abnormally (e.g., chromosome number, cytoskeleton formation) in culture compared to in vivo conditions. Additionally, current culture methods utilize high doses of animal proteins, like serum, which may result in an oversized fetus and perinatal complication for the offspring.

Some of the difficulties in assisted reproduction technologies can be overcome by coculturing sperm, oocytes and embryos with cell feeder layers. However, cocultures are of variable quality and variable reliability and add the risk of pathogen transfer from the feeder cells to the gametes or embryos that are to be transferred back to living animals or humans.

Storage of sperm is of widespread importance in commercial animal breeding programs, human sperm donor programs and in dealing with some disease states. For example, sperm samples may be frozen for men who have been diagnosed with cancer or other diseases that may eventually interfere with sperm production. Freezing and storage of sperm is critical in the area of preservation of endangered species. Many of these species have semen which does not freeze well under existing methods. In standard animal husbandry, artificial insemination (AI) with frozen bull sperm is used in 85% of dairy cows. Because most commercial turkeys have become too heavy to mate naturally, AI is required on almost all turkey farms. Approximately six million turkey hens are inseminated each week in the United States. However, existing methods of storing collected turkey sperm cannot support sperm survival for even the several hours required to transport semen between farms, much less for long-term freezing. This limits the ability to store or transport genetic material to improve production. Human donor AI is also used for couples with severe male infertility; however, pregnancy rates with donor semen in people is only a quarter of that found with natural reproduction. Furthermore, surgical insemination may be required.

Current techniques for freezing sperm from all species result in membrane damage and subsequent death of about half of the sperm cells in a sample. Much of this damage occurs by reactive oxygen species causing lipid peroxidation of the sperm membrane. Despite these widespread and serious problems, the state of the art and protocols for this field have changed very little in the last 15 years. In light of the increasing use of frozen sperm in a variety of settings, a new method of freezing or storing sperm would offer a major breakthrough for human fertility specialists, animal producers, and conservation specialists.

Freezing oocytes and embryos is also important for preserving genetic material from endangered species, increasing offspring production from valuable livestock individuals, or for retaining embryos for infertile couples prior to transfer. Current methods of freezing oocytes and embryos are less than optimal with decreased development potential seen. In fact, human oocytes are rarely successfully frozen, necessitating placing multiple embryos into a woman's uterus which increases the number of dangerous and high risk multiple pregnancies. In addition, IVF embryos or genetically altered embryos from all species, such as those obtained after gene therapy, have very poor post-freezing survival rates with existing freezing media. This includes cloned embryos and embryos derived from embryonic stem cells (ESC).

For couples with fertility problems, an alternative course to the assisted reproduction techniques described above for improving the chance of conception is to have multiple, timed events of coitus during oocyte ovulation. For many of these couples, the emotional stress of infertility and the necessity of timed coitus month after month can lead to the need for artificial lubrication during intercourse. However, most commercially available lubricants are spermicidal, as is saliva, so that infertile couples are often instructed by their physician to not utilize any lubricant products during intercourse. In addition, many aspects of reproductive medicine in both humans and animals would be enhanced by the use of non-spermicidal lubrication during procedures such as manual sperm sample collection, artificial insemination, and uterine catheterization. The lubricant products on the market are not acceptable for use in these situations because of their spermicidal properties.

Following deposition in the female, sperm must penetrate the cervical mucus of the female and swim to the oviducts (Fallopian tubes) where they remain until ovulation and fertilization occurs. Sperm that are compromised may not be able to swim through this mucus and are thus not available for the fertilization process, limiting the fertility of the male. Furthermore, sperm that are slow to enter the cervical mucus are left in contact with the vaginal mucosa which is acidic and can inactivate sperm within several hours. Sperm with impaired fertilization potential include those that have been frozen, those where the male has antibodies in his semen that weaken the sperm, or sperm that have abnormal motion or shapes. Therapeutic options for treating male factor infertility, which accounts for 60% of infertility cases, are currently very limited and often end up utilizing very expensive intervention techniques, such as ICSI in which a single sperm is injected into an egg. As well, an increased incidence in genetic and/or birth defects have been reported for offspring from such sperm injection techniques. A product that improves sperm survival, motility and mucus penetration after ejaculation or insemination in the female could increase the number of sperm available in the oviduct for fertilization and thus could improve the chances of conception occurring without invasive intervention.

The present invention provides a variety of compositions that are non-toxic to sperm, oocytes or embryos, which additionally improve their function and survival during in vitro handling and which improve sperm function for use by couples trying to conceive naturally, as well as for use in a variety of assisted reproduction techniques in humans and animals. The present invention further provides other related advantages.

SUMMARY OF THE INVENTION

The present invention provides methods and compositions for improving the function of germ cells (sperm and oocytes), and embryos both in vivo and in vitro.

Within one aspect, methods for isolation of motile sperm having improved function are provided comprising contacting a sample containing sperm with a solution comprising a polysaccharide containing arabinose, galactose and/or hexuronic acid (PCAGH) to form a mixture, wherein the PCAGH is not arabinogalactan, and then removing the wash solution. This mixture is subjected to conditions sufficient to separate the motile sperm from the rest of the sample, thereby isolating the sperm with improved function. In a related aspect, methods for washing sperm to remove the nonsperm portion of a sample and to obtain sperm with improved function are provided comprising contacting a sample containing sperm with a solution comprising a polysaccharide containing arabinose, galactose and/or hexuronic acid, wherein the PCAGH is not arabinogalactan, and removing the wash solution. Within certain embodiments, the polysaccharide is pectin, arabic acid, gum arabic, gum ghatti, gum karaya, gum guar, galactopyranosylarabinose, galacturonic acid, gum locust bean, gum tragacanth, carrageenan, or derivatives thereof. Within another embodiment, the sample is semen. Within yet other embodiments, the sample is obtained from human, bovine, canine, equine, porcine, ovine, avian, rodent or exotic species. In certain embodiments, it may also include other density gradient compounds, such as dextran, iodixanol, sucrose polymers, nycodenz, or polyvinylpyrrolidine coated silica (Percoll). In other embodiments, the solution comprises a balanced salt solution and a macromolecule.

Within another aspect, a sperm wash medium is provided comprising a polysaccharide containing arabinose, galactose and/or hexuronic acid (PCAGH) and a macromolecule wherein the PCAGH is not arabinogalactan. The polysaccharide is present at a concentration sufficient to improve sperm function at 1–50%. In certain embodiments, the macromolecule is gelatin, bovine serum albumin, human serum albumin, egg yolk, oviductin, polyvinyl alcohol, hyaluronic acid, gelatin, catalase, or casein. Generally, the solution further comprises a balanced salt solution.

Within a related aspect, a medium for the isolation of motile sperm from a sample is comprised of a PCAGH at 0.01–5% and a density gradient compound for centrifugation isolation, or a macromolecule for swim-up separation.

Within another related aspect, an extending medium for sperm is provided comprising a PCAGH in a solution at a concentration sufficient to improve sperm function.

In another aspect, a non-spermicidal lubricant for increasing fertilization potential in animals is provided comprising a non-spermicidal lubricious compound and a polysaccharide containing arabinose, galactose and/or hexuronic acid (PCAGH). Within certain embodiments, the lubricious compound comprises glycerine, methylcellulose, propylene glycol, plant oils, or petroleum jelly, or a combination of glycerin and petroleum jelly, or a combination of polyethylene oxide, sodium carboxypolymethylene and methylparaben. Within other embodiments, the polysaccharide is pectin, arabinogalactan, arabic acid, gum arabic, gum ghatti, gum karaya, gum guar, galactopyranosylarabinose, galacturonic acid, gum locust bean, gum tragacanth, carrageenan, or a derivative thereof. The lubricant may be used in vivo by administration or placement in a vagina prior to coitus or artificial insemination, or used during semen collection, such as by applying the lubricant to a penis prior to ejaculation into a receptacle or collecting sperm into a receptacle containing the lubricant. In a related aspect, the lubricant is used to lubricate medical devices or a hand prior to reproductive procedures.

In yet other aspects of the subject invention, methods for increasing the survival of sperm, oocyte, embryo and embryonic stem cells in vitro are provided comprising contacting a sample containing one of the cell types with a medium acceptable to the cell and including a polysaccharide containing arabinose, galactose and/or hexuronic acid (PCAGH). Within certain preferred embodiments, the medium is a balanced salt solution medium. Within other embodiments, the medium further comprises a macromolecule, such as blood serum, synthetic serum supplements, bovine serum albumin, human serum albumin, oviductin, superoxide dismutase, vitamin E, gelatin, polyvinyl alcohol, hyaluronic acid, catalase, chondroitin sulfate, heparin, egg yolk, skim milk, casein, melanin, hormone or growth factors. With other embodiments, the medium also comprises a sperm stimulant. Sperm stimulants include caffeine, follicular fluid, oxytocin, kallikrien, prostaglandins, thymus extract, pentoxyfilline, deoxyadenosine, inositol, platelet activating factor, hypotaurine, or mercaptoethanol.

Within yet other aspects, methods for reducing the loss of functional sperm, reducing the cellular damage to an oocyte, and reducing the cellular damage to an embryo or embryonic stem cell (ESC), resulting from the storage of the cells in a refrigerated, frozen or vitrified state are provided. More specifically, a polysaccharide containing arabinose, galactose and/or hexuronic acid (PCAGH) and a sample containing sperm, oocyte, or embryo, are combined wherein the polysaccharide is in an amount effective to reduce the loss or damage and the sample is then stored in a refrigerated, frozen or vitrified state. Within certain preferred embodiments, an additional cryoprotective compound is added. Within a related aspect, a medium for storing sperm, oocytes, or embryos is provided comprising a balanced salt solution and a polysaccharide containing arabinose, galactose and/or hexuronic acid.

These and other aspects of the invention will become evident upon reference to the following detailed description and attached drawings. In addition, various references are set forth below which describe in more detail certain procedures or compositions. Each of these references are incorporated herein by reference in their entirety as if each were individually noted for incorporation.

DETAILED DESCRIPTION OF THE INVENTION

Figure 1:
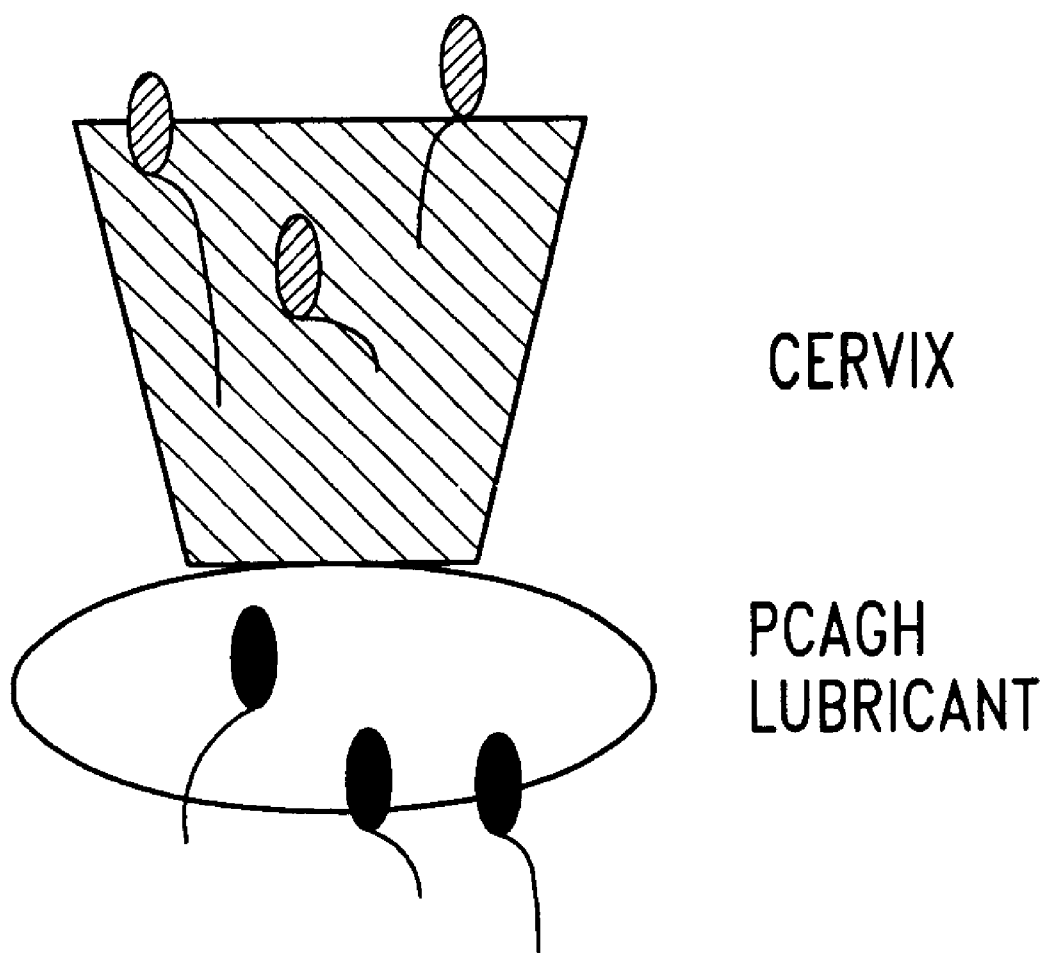
FIG. 1 is a drawing depicting an anatomic overview of how a lubricant containing a polysaccharide containing arabinose, galactose and/or hexuronic acid (PCAGH) may be used.

Prior to setting forth the invention, it may be helpful to an understanding thereof to set forth definitions of certain terms that will be used hereinafter.

As used herein, "polysaccharides containing arabinose, galactose and/or hexuronic acid" (hereinafter referred to "PCAGH") refers to a polymer comprising arabinose and galactose or hexuronic acid or combinations thereof (e.g., a hexuronic acid and galactose or arabinose or both). A monomeric unit of a hexuronic acid (e.g., galacturonic acid) may also be used within the context of the present invention. When the polysaccharide comprises arabinose and galactose, at least a disaccharide must be present. Generally, however, PCAGHs have a molecular mass in the range of 6 kDa to 1500 kDa. The PCAGH may contain other saccharides as well, or other molecules such as proteins, peptides, lipids, nucleic acids and the like. Examples of a PCAGH include, but are not limited to arabinogalactan, pectin, arabic acid, gum arabic, fucoidan, funoran, iridophycan, gum ghatti, gum tragacanth, quince seed gum, plantago polysaccharide, psyllium seed, flax seed gum, gum karaya, gum guar, locust bean gum, carrageenan, seaweed extracts, plant or root extracts from *Gymnema sylvestre, Helianthus annuus* L., *Angelica acutiloba, Ariemisia princps, Bupleurum Falatum* L. *Panax ginseng, Malva sylvestris* var. mauritiana, *Rubus fruticosus* and *Hibiscus sabdariffa;* polysaccharides from microorganisms, polysaccharides from plant cell cultures, or derivatives of the above. As used herein, a "hexuronic acid" is a tetrahydroxy aldehyde acid obtained generally by oxidation of hexose sugars. Such hexuronic acids include glucuronic acid, galacturonic acid, mannuronic acid, guluronic acid, iduronic acid, and the like (see, "Carbohydrates," ed. P. M. Collins, Chapman and Hall, NY, 1987; Merck Index).

As used herein, "improved function" of sperm refers to the improved potential of a sperm to fertilize an oocyte. This potential may be assessed by motility, viability, survival time, membrane stabilization, levels of lipid peroxidation damage, chromatin stability, mucus penetration, oocyte fertilization or subsequent embryonic development and the like. Likewise, "improved function" of an oocyte refers to the improved potential for fertilization of the oocyte by sperm, followed by normal development. "Improved function" of an embryo refers to improved potential for normal development and offspring production. This potential for oocytes and embryos is assessed by evaluating chromosome numbers, cell numbers, cytoskeleton formation and metabolic activity. "Improved function" means that the sperm, oocyte or embryo have enhanced performance as assessed by one of these assays when treated with a PCAGH under conditions described herein as compared to a control (i.e., no treatment with a PCAGH).

As used herein, "embryo" refers to an animal in early stages of growth following fertilization up to the blastocyst stage. An embryo is characterized by having totipotent cells, which are nondifferentiated. In contrast, somatic cells of an individual are cells of a body that are differentiated and are not totipotent.

As used herein "embryonic stem cell" (ESC) refers to established cultured cell lines originating from a single embryo. ESCs are a population of cells having identical genetic material. Each cell is totipotent and, if fused with a nonfertilized oocyte, generates genetically identical animals.

I. Polysaccharides Containing Arabinose, Galactose and/or Hexuronic Acid

As described above, a polysaccharide containing arabinose, galactose and/or hexuronic acid ("PCAGH") refers to a polymer containing at least arabinose and/or galactose units in combination with a hexuronic acid or to the hexuronic acid alone (e.g., galacturonic acid). Preferred PCAGHs contain arabinose, galactose and galacturonic acid. These polysaccharides generally occur in nature as water soluble polymers obtained from the gum or pectic fractions of plants. Such substances are also released by plant cells and microbial cells in culture (Bushel et al., *Food Hydrocolloids* 1:359–363, 1987). Chemical and enzymatic fractionation of PCAGHs provide active fractions that are also useful in the present invention (see, Examples). The PCAGHs or their derivatives may be chemically synthesized in vitro. In addition, derivatives obtained through refinements such as acid or heat (e.g., autoclaving) treatments of these PCAGHs, are also useful in the present invention, examples being production of arabic acid from gum arabic and production of small molecular weight derivatives from arabinogalactan via autoclaving. Glycoproteins may also be used if they contain an active fraction. PCAGHs are commercially available in a variety of forms, such as arabinogalactan, pectin, arabic acid and gum arabic (Sigma, St. Louis, Mo.; GlycoTech, Rockville, Md.; Seikagaku, Ijamsville, Md.; Accurate Chemical Co., Westbury, N.Y.; Boehringer Mannheim, Indianapolis, Ind.).

Pectic substances, more commonly referred to as pectins, are a complex mixture of polysaccharides characterized by a backbone of $\alpha(1\rightarrow 4)$ linked galacturonic acid units that are partially methyl-esterified (O'Neill et al., *Methods in Plant Biochemistry* 2:415–441, 1990). All pectins contain some associated neutral sugars, such as L-arabinose, D-galactose, L-rhamnose, D-xylose and D-glucose. Chemical and enzymatic degradation of pectins reveal long and regular uronic regions (smooth) and rhamnose-rich regions (hairy) that have neutral sugars as side chains. Pectins are present in the primary cell walls of all seed-bearing plants and are major components of dicotyledons (e.g., citrus and legumes) and gymnosperms (e.g., Douglas fir). Commercially important sources of pectin sources include apple and citrus pulps (e.g., Sigma Chemical Co., St. Louis, Mo.), sugar beet, and alfalfa.

Gum exudates are viscous fluids that are discharged from plants and contain high levels of polysaccharides. Gums are also found in various seeds, seaweed, and microbial cultures. These gums comprise polysaccharides that are complex and highly branched with residues of hexuronic acids (typically D-glucuronic acid and/or galacturonic acid) along with neutral sugars (Aspinall, *The Carbohydrates,* ed. W. Pigman, and D. Horton, Ch. 39:515–536, 1970). Examples of gums that contain PCAGHs include gum arabic, gum tragacanth, gum ghatti, gum karaya, and larch arabinogalactan. Arabinogalactans are found in most plants and are present as side chains in many gums and pectic complexes (Clarke et al., *Phytochemistry* 18:521–540, 1979). The Type II arabino-3,6-galactans have been detected in seeds, leaves roots, fruit and gum exudates. Arabinogalactan from the mountain larch has a $\beta$-D$(1\rightarrow 3)$ linked galactopyranosyl backbone with 1,6 linked side chains. Derivatives of arabinogalactan, such as amino derivatives, succinyl-arabinogalactan, glutaryl-arabinogalactan, arabinogalactan hydrazide, phosphoryl arabino-galactan and the like, may be used in the present invention (see, for example, PCT application WO 93/25239). Gum arabic, an exudate from Acacia senegal is regarded as representative of exudate gums that have a core composed of branched chains of D-galactopyranose residues. Gum arabic also typically contains residues of L-arabinose, D-galactose, L-rhamnose and D-glucuronic acid. Arabic acid is an acid-ethanol precipitate derivative of gum arabic. Many of these gums can be obtained commercially (e.g., Sigma Chemical Co., St. Louis, Mo.).

Hexuronic acids are 6 carbon sugars with a COOH group. The sugar may be linear or ring-structured. Side groups may be present in addition. Hexose sugars that may be oxidized include glucose, galactose, mannose, gulose, idose, talose, altrose, and allose. Common hexuronic acids include glucuronic acid, galacturonic acid, and mannuronic acid. (See, "Carbohydrates" supra; Merck Index for others.)

Other PCAGHs include, for example, fucoidan, femoral, iridophycan, quince seed gum, plantago polysaccharide from psyllium seed, flax seed gum, gum guar, locust bean gum, carrageenan, seaweed extracts; plant or root extracts from *Gymnema sylvestre, Helianthus annuus* L., *Angelica acutiloba, Ariemisia princps, Bupleurum Falatum* L. *Panax ginseng, Malva sylvestris* var. mauritiana, *Rubus fruticosus* and *Hibiscus sabdariff*, polysaccharides from microorganisms; polysaccharides from plant cell cultures; or active derivatives of the above.

Other PCAGHs may be obtained through derivation of naturally-derived pectic substances and gums by chemical and enzymatic means (see, in general, *The Carbohydrates*, Ch. 39, ed. W. Pigman et al., Academic Press, N.Y. and London, 1970; *Methods in Plant Biochemistry* 2:415, 1990; Stephen et al., *Methods in Plant Biochemistry* 2:483, 1990; Lau et al., *Carb. Res.* 168:219, 1987). Acid hydrolysis and heat autolysis procedures yield small oligomeric derivatives with biological activity. Polygalacturonic oligomers have been synthesized (Nakahara and Ogawa, *Carbohydrate Research* 200:363–375, 1990) and chemically modified (Moloshok et al., *Archives of Biochemistry and Biophysics* 294(2):731–734, 1992). Also encompassed are gums that have been modified through the introduction of neutral groups to increase solution viscosity; the addition of methyl, ethyl, hydroethyl and similar groups; the introduction of acidic groups; the introduction of graft polymers; or modification by thermal dextinization, partial hydrolysis and mild oxidation. Modification may be performed using, for example, pectinase, endoarabinanase, $\alpha$-L-arabinofuranosidase, and endopolygalacturonase. Enzymes are commercially available (e.g., Megazyme, Bozeman, Mon.; Seikagaku, Ijamsville, Md.; GlycoTech, Rockville, Md.; Sigma, St. Louis, Mo).

PCAGHs may be identified by degradation procedures, including acid hydrolysis, enzymatic digestion, combined with detection methods (e.g., GC, mass-spectrometry, TLC, NMR, IR spectroscopy) for the monomeric sugars or uronic acids. Other commonly employed methods to identify saccharides may be interchangeably substituted (see, for example, Müller and Franz, *Planta Med* 58:60, 1992; Gonda et al., *Carb. Res.* 198:323, 1990; Wicken and Leiting, *Anal. Biochem.* 229:148, 1995; Taylor and Buchanan-Smith, *Anal. Biochem.* 201:190, 1992; Bach and Schollmeyer, *Anal. Biochem.* 203:335, 1992; Ló et al., *Carb. Res.* 255:271, 1994; de Vries et al., *Carb. Polymers* 3:193, 1983; McCleary and Matheson, *Adv. in Carb. Chem. Biochem.* 44:147, 1986; Leitão et al., *Carb. Polymers* 26:165, 1995; Eagles et al., *Phyto. Chem.* 34:709, 1993; Selvendran and Rydan, *Methods in Plant Biochemistry* 2:549, 1990).

The various polysaccharides exhibit widely different degrees of water solubility. In general, polysaccharides with high solubility are soluble to about 60% before the viscosity makes the solution essentially unworkable. Low solubility polysaccharides are soluble to about 10% or less before the viscosity makes the solution essentially unworkable. High solubility polysaccharides include arabinogalactan and gum arabic. Low solubility polysaccharides include pectin and arabic acid.

II. Improved Sperm Function

As noted above, improved sperm function refers to the increased capability of sperm to fertilize an oocyte. This function may be assayed by a broad range of measurable cell functions. Such assayable functions include sperm motility, sperm viability, membrane integrity of sperm, in vitro fertilization, sperm chromatin stability, survival time in culture, penetration of cervical mucus, as well as sperm penetration assays and hemizona assays. Sperm have improved function after exposure to a composition or method if they perform significantly better ($p<0.05$) with a PCAGH under conditions described herein as compared to a control (i.e., assay performed without including a PCAGH). A brief description of various assays that may be used to assess sperm function are presented herein. These assays are provided as exemplary techniques; variations or alternative methods that measure the tested functions may be used.

Sperm motility is one function that may be used to assess sperm function and thus fertilization potential. Motility of sperm is expressed as the total percent of motile sperm, the total percent of progressively motile sperm (swimming forward), or the speed of sperm that are progressively motile. These measurements may be made by a variety of assays, but are conveniently assayed in one of two ways. Either a subjective visual determination is made using a phase contrast microscope when the sperm are placed in a hemocytometer or on a microscope slide, or a computer assisted semen analyzer is used. Under phase contrast microscopy, motile and total sperm counts are made and speed is assessed as fast, medium or slow. Using a computer assisted semen analyzer (Hamilton Thorn, Beverly, Mass.), the motility characteristics of individual sperm cells in a sample are objectively determined. Briefly, a sperm sample is placed onto a slide or chamber designed for the analyzer. The analyzer tracks individual sperm cells and determines motility and velocity of the sperm. Data is expressed as percent motile, and measurements are obtained for path velocity and track speed as well.

Sperm viability is measured in one of several different methods. By way of example, two of these methods are staining with membrane exclusion stains and measurement of ATP levels. Briefly, a sample of sperm is incubated with a viable dye, such as Hoechst 33258 or eosin-nigrosin stain. Cells are placed in a hemocytometer and examined microscopically. Dead sperm with disrupted membranes stain with these dyes. The number of cells that are unstained is divided by the total number of cells counted to give the percent live cells. ATP levels in a sperm sample are measured by lysing the sperm and incubating the lysate with luciferase, an enzyme obtained from fireflies, which fluoresces in the presence of ATP. The fluorescence is measured in a luminometer (Sperm Viability Test; Firezyme, Nova Scotia, Canada). The amount of fluorescence in the sample is compared to the amount of fluorescence in a standard curve allowing a determination of the number of live sperm present in the sample.

Membrane integrity of sperm is typically assayed by a hypo-osmotic swell test which measures the ability of sperm to pump water or salts if exposed to non-isotonic environments. Briefly, in the hypo-osmotic swell test, sperm are suspended in a solution of 75 mM fructose and 25 mM sodium citrate, which is a hypo-osmotic (150 mOsm) solution. Sperm with intact, healthy membranes pump salt out of the cell causing the membranes to shrink as the cell grows smaller. The sperm tail curls inside this tighter membrane. Thus, sperm with curled tail are counted as live, healthy sperm with normal membranes. When compared to the total number of sperm present, a percent of functional sperm may be established.

The degree of membrane integrity is preferably determined by lipid peroxidation (LPO) measurements which assess sperm membrane damage generated by free radicals released during handling. Lipid membrane peroxidation is assayed by incubating sperm with ferrous sulfate and ascorbic acid for one hour in a 37° C. water bath. Proteins are precipitated with ice-cold trichloroacetic acid. The supernatant is collected by centrifugation and reacted by boiling with thiobarbituric acid and NaOH. The resultant malondialdehyde (MDA) formation is quantified by measuring absorbance at 534 nm as compared to an MDA standard (M. Bell et al., *J. Andrology* 14:472–478, 1993). LPO is expressed as nM MDA/$10^8$ sperm. A stabilizing effect of PCAGHs results in decreased LPO production.

The stability of chromatin DNA is assayed using the sperm chromatin sensitivity assay (SCSA). This assay is based on the metachromatic staining of single and double stranded DNA by acridine orange stain, following excitation with 488 nm light. Green fluorescence indicates double strand DNA, and red fluorescence indicates single strand DNA. The extent of DNA denaturation in a sample is expressed as $\alpha$ and calculated by the formula $\alpha=\text{red}/(\text{red}+\text{green})$. In all cases, sperm are mixed with TNE buffer (0.01 M Trisaminomethane-HCl, 0.015M NaCl, and 1 mM EDTA) and flash frozen. Sperm samples are then subjected to 0.01% Triton-X, 0.08N HCl and 0.15M NaCl, which induces partial denaturation of DNA in sperm with abnormal chromatin. Sperm are stained with 6 g/ml acridine orange and run through a flow cytometer to determine $\alpha$.

In vitro fertilization rates are determined by measuring the percent fertilization of oocytes in vitro. Maturing oocytes are cultured in vitro in M199 medium plus 7.5% fetal calf serum and 50 μg/ml luteinizing hormone for 22 hours. Following culture for 4 hours, the sperm are chemically capacitated by adding 10 IU of heparin and incubated with oocytes for 24 hours. At the end of the incubation, oocytes are stained with an aceto-orcein stain or equivalent to determine the percent oocytes fertilized. Alternatively, fertilized oocytes may be left in culture for 2 days, during which division occurs and the number of cleaving embryos (i.e., 2 or more cells) are counted.

Survival time in culture of sperm (time to loss of motility) is another convenient method of establishing sperm function. This parameter correlates well with actual fertility of a given male. Briefly, an aliquot of sperm is placed in culture medium, such as Tyrode's medium, pH 7.4 and incubated at 37° C., 5% $CO_2$, in a humidified atmosphere. At timed intervals, for example every 8 hours, the percentage of motile sperm in the culture is determined by visual analysis using an inverted microscope or with a computer assisted sperm analyzer. As an endpoint, a sperm sample is considered no longer viable when less than 5% of the cells have progressive motility.

Another parameter of sperm function is the ability to penetrate cervical mucus. This penetration test can be done either in vitro or in vivo. Briefly, in vitro, a commercial kit containing cervical mucus (Tru-Trax, Fertility Technologies, Natick, Mass.), typically bovine cervical mucus, is prepared. Sperm are placed at one end of the track and the distance that sperm have penetrated into the mucus after a given time period is determined. Alternatively, sperm penetration of mucus may be measured in vivo in women. At various times post-coitus, a sample of cervical mucus is removed and examined microscopically for the number of sperm present in the sample. In the post-coital test, improved sperm function is established if more sperm with faster velocity are seen in the mucus sample after exposure to a PCAGH lubricant versus a sample of mucus from the patient after exposure to a control lubricant.

Other assays of sperm function potential include the sperm penetration and hemizona assays. In the sperm penetration assay, the ability of sperm to penetrate into an oocyte is measured. Briefly, commercially available zona free hamster oocytes are used (Fertility Technologies, Natick, Mass.). Hamster oocytes are suitable in this assay for sperm of any species. Capacitated sperm, such as those cultured with bovine serum albumin for 18 hours, are incubated for 3 hours with the hamster oocytes. Following incubation, oocytes are stained with acetolacmoid or equivalent stain and the number of sperm penetrating each oocyte is counted microscopically. A hemizona assay measures the ability of sperm to undergo capacitation and bind to an oocyte. Briefly, in this assay, live normal sperm are incubated in media with bovine serum albumin, which triggers capacitation. Sperm are then incubated with dead oocytes which are surrounded by the zona pellucida, an acellular coating of oocytes. Capacitated sperm bind to the zona and the number of sperm binding is counted microscopically.

III. Lubricants

As noted above, within one aspect of the present invention, PCAGHs are formulated as a nonspermicidal lubricant for improving sperm function and potential fertility in animals. The lubricants comprise a base containing a lubricious compound, which is nonspermicidal, and a PCAGH.

The base of the lubricant is a nonspermicidal lubricious compound. Such lubricants include petroleum jelly, vegetable oil, glycerin, polycarbophil, hydroxyethyl cellulose, methylcellulose, silicon oil, carbomer (e.g., carbomer 934), alginate, methylparaben, palm oil, cocoa butter, aloe vera, other plant oils, alginate propylene glycol, unibase (Warner-Chilcott), mineral oil, a combination of polyethylene oxide, sodium carboxypolymethylene and methylparaben, and the like. A base lubricant of 50% petroleum jelly/50% glycerin is preferred. Additional ingredients, such as pH stabilizers and anti-oxidants, may be added. Sodium hydroxide is preferably added to bring the pH to 7.4. Other pH stabilizers include EDTA or zwitterionic buffers (e.g., TES, PIPES, MOPS, HEPES). Anti-oxidants, or free-radical scavengers such as vitamin E, may be added. In certain embodiments, silicon oil or polyvinyl alcohol are added.

A PCAGH is added to the lubricious compound to 0.01–40% (e.g., 0.01–30%; 0.01–20%), preferably to 0.1 to 5% for high viscosity polysaccharides, and most preferably to 0.1 to 1%; preferably to 1–20% for low viscosity polysaccharides, and most preferably to 10–20%. Examples of preferred embodiments include 0.1% pectin, 1% galacturonic acid, 1% gum guar, 10% gum arabic, or 20% arabinogalactan.

The lubricant is preferably non-irritating and easily applied. It may be in the form of a gel, foam, cream, jelly, suppository (see, e.g., U.S. Pat. No. 4,384,003 to Kazrmiroski), or the like. The lubricant may be packaged in a kit containing a tube of lubricant and an applicator for intra-vaginal application. For use during coitus or artificial insemination, the lubricant may be applied intra-vaginally. It may also be applied to a penis for use during intercourse or for collection of sperm. Generally, sperm donors collect sperm samples by manual manipulation without the benefit of lubrication because available lubricants and saliva are spermicidal. The lubricant of the present invention may be applied directly to the penis, coat the interior or exterior of a condom, or be placed in a receptacle for sperm collection such as a vial, tube, baggie, or other collection device.

In addition, the lubricant may be used in various assisted reproductive techniques and diagnostic procedures. For example, the lubricant may be used to coat a catheter for insertion into a bladder to collect sperm from a retrograde ejaculation. It may be used to lubricate a catheter, pipette or hand, prior to performing embryo transfer, artificial insemination, or diagnostic procedures such as endoscopy, contrast radiography or biopsy. The lubricant may be used in any animal species for sperm collection, coitus, assisted reproductive techniques and the like. Such animals include, but are not limited to, humans, bovine, equine, canine, ovine, avian, feline, and various exotic or rare species (e.g., elephant, lion, rhinoceros).

IV. Isolating and Washing Sperm

In other aspects of this invention, methods are provided for washing and isolating sperm and sperm-containing samples to obtain sperm-rich samples and samples of the most motile sperm. Such samples contain sperm with improved function. Sperm are washed by contacting a sample containing sperm with a solution containing a PCAGH, wherein the polysaccharide is not arabinogalactan. Motile sperm are isolated by contacting a sample containing sperm, such as an ejaculate, with a media solution comprising a PCAGH, wherein the polysaccharide is not arabinogalactan, and subjecting the mixture to conditions sufficient to separate the sperm.

For all these methods, the PCAGH is preferably added to a standard balanced salt solution. Such media include, but are not limited to, Tyrode's albumin lactate phosphate (TALP), human tubal fluid (HTF; Fertility Technology, Natick, Mass.), Ham's F10, Ham's F12, Earle's buffered salts, Biggers, Whitten and Whitingham (BWW), CZB, T6, Earle's MTF, KSOM, SOF, and Benezo's B2 or B3 media. Formulas for these media are well known, and preformulated media may be obtained commercially (e.g., Gibco Co. or Fertility Technologies, Natick, Mass.). In addition, a zwitterionic buffer (e.g., MOPS, PIPES, HEPES) may be added. The PCAGH includes, but is not limited to, any of the polysaccharides discussed above. Preferably the PCAGH is pectin, gum guar, or gum arabic for isolating and washing sperm. Wash media contain PCAGH at concentrations of about 1–50% (e.g., 5–30%; 5–20%; 10–20%). In preferred embodiments, gum arabic is added to about 20% or gum guar is added to about 5%. In another embodiment, galacturonic acid is added.

These media may further contain a macromolecule as long as the solution remains a balanced salt solution. Such macromolecules include polyvinyl alcohol, albumin (bovine serum albumin or human serum albumin), oviductin (Gandolfi et al., *Repro. Fert. Dev.* 5:433, 1993), superoxide dismutase, vitamin E, gelatin, hyaluronic acid, catalase, egg yolk, casein, or other protein. Albumin or gelatin is added generally at 0.5% and hyaluronic acid or polyvinylalcohol at 1.0%; the other macromolecules are added at similar concentrations (e.g., 0.05–5%). Sperm isolation media contain at least one PCAGH at about 0.01–5% (e.g., 0.1–5%, 0.1–1%, 1%–5%) in addition to either a density gradient compound for centrifugation methods, or a macromolecule for swim-up isolation methods. Density gradient materials are generally added to a concentration of 5–90%. Such materials include dextran, iodixanol, sucrose polymers, nycodenz, or polyvinylpyrrolidone coated silica (i.e., Percoll). In typical applications, a sperm containing solution is layered over a gradient material, preferably Percoll at 30–90% mixed with 0.05% pectin, and then subjected to centrifugation to collect sperm with improved function. When sperm swim-up is used to isolate sperm, a macromolecule, such as those discussed above, is added. Preferably 1–10 mg/ml of hyaluronic acid is used. A preferred medium is PCAGH at 0.01–5% (e.g., 0.05% gum arabic or 1% galacturonic acid) in combination with hyaluronic acid. Media used in any of these procedures may further comprise a balanced salt solution.

As noted above, sperm are washed or isolated by contacting a sample with a solution comprising a PCAGH, wherein the polysaccharide is not arabinogalactan, and subjecting the mixture to conditions sufficient to separate the desired sperm from the sample. Briefly, cells are contacted with the solution by placing cells in the solution from a brief time up to incubation for 4 hours. Preferably the temperature at which contacting occurs is from about 20° C. to about 39° C. Following this initial contact, different methods may be used to isolate sperm, such as centrifugation, swim-up, separation columns, and the like. For example, one such method is centrifugation of a sperm sample through a continuous gradient of the solution comprising a PCAGH. In this method, the solution comprising a PCAGH is placed in a centrifuge tube and a semen sample or sperm cells are layered over the medium at approximately a ratio of one part semen (or sample) to one part medium. The tube is centrifuged at approximately 300×g for ten to twenty minutes. A sperm-rich fraction with improved function, and thereby increased fertilization potential, is recovered in a pellet at the bottom of the tube. Because the PCAGH is non-toxic to sperm, a follow-up wash step to remove the PCAGH is not required. Isolation may be performed in a method similar to the above wash process; however, the PCAGH solution can either be layered under the sperm sample, but on top of a density gradient like Percoll, or mixed directly into the Percoll gradient. Alternatively, sperm are isolated by a swim-up method. Briefly, sperm swim-up tubes are prepared by placing 1.5 ml of wash media in a 12×75 mm round bottom tube. Sperm are layered under this wash media using a 27 gauge needle and 1 ml syringe at 1 part sperm suspension to 2 parts wash medium. The tubes are incubated undisturbed for 1 hr. After incubation, the wash medium (that the motile sperm have swum up into) is removed and centrifuged for 10 min at 300×g. A final pellet of motile sperm is then recovered for analysis or use. Other methods, such as column separation, may alternatively be used.

Sperm may be further washed after isolation of sperm by the methods described herein or by other methods used, such as centrifugation through a Percoll gradient. Washing sperm can be used to transfer sperm from one solution to another comprising a PCAGH.

For any of these methods, the sample may be semen, partially purified sperm, or purified sperm. Moreover, sperm suitable in the present invention may be procured from animal species including human, bovine, canine, equine, porcine, ovine, rodent, avian or exotic animals, such as lions, tigers, giraffes, monkeys, zebras, pandas, jaguars, elephants, rhinoceros, and others.

V. Extending and Culturing Sperm Cells and Culturing Oocytes or Embryos

In other aspects of this invention, methods for extending sperm (e.g., to dilute or suspend the sperm) to obtain sperm with improved function are provided. Sperm are extended by addition of a solution comprising a PCAGH. The concentration of PCAGH for extending sperm is from 0.001–5% (0.01–5%; 0.05–1%; 0.05–0.5%). For example, pectin, gum ghatti, or gum arabic are added at 0.05%; gum guar, galacturonic acid, or galactopyranosylarabinose at 0.1%; and arabic acid or arabinogalactan at 0.5%. Galacturonic acid may also be used alone or with other PCAGH at 0.01–5.0% (e.g., 0.01%–1%; 0.05–0.5%; 0.1–1%).

Extending sperm is used to resuspend a sperm pellet following isolation or washing, to dilute a semen sample, to dilute a culture of sperm, and the like. In this way, sperm are placed into a medium suitable for a variety of procedures, including culture, insemination, assays of fertilization potential as described herein, in vitro fertilization, freezing, intrauterine insemination, cervical cap insemination, and the like. The sperm may be added to the medium or the medium may be added to the sperm. Preferably, the medium contains gum guar, gum arabic, pectin or galacturonic acid, although another PCAGH may be used. In other aspects of this invention, methods are provided for the culture of such extended sperm to increase their survival during holding or culture at a range of temperatures from about room temperature (e.g., 20° C.) to about body temperature (e.g., 37° C. or 39° C.). This includes culture of sperm in toxicity screen tests and the holding of sperm for sorting into X and Y chromosome-containing fractions by flow cytometry for generating sexed offspring. In other aspects of this invention, sperm extending medium is used for preparing sperm for direct insemination, cryopreservation, and for intracytoplasmic sperm injection (ICSI) which requires a more viscous media to slow motile sperm down for pick-up by the transfer pipette for injection into the egg. In ICSI, the medium contains PCAGH at higher levels than a routine extender medium (i.e., 1% arabic acid or 5% gum arabic) to increase viscosity. A viscous solution of PCAGH also has a positive effect on sperm function by limiting membrane damage and possible chromatin breakdown during in vitro handling. Additional embodiments include encapsulation of the sperm (Munkittrick et al., *J. Diary Sci.* 75:725–731) in an alginate or protamine sulfate microcapsule containing PCAGH, such as pectin at 0.05%. Encapsulation allows for shedding of sperm over an increased time frame so that insemination does not have to be as well timed with ovulation. PCAGH stabilizes sperm membranes from breakdown observed with current procedures.

For all these methods, except encapsulation, the polysaccharide containing arabinose, galactose and/or hexuronic acids is preferably added to a balanced salt solution which may contain zwitterionic buffers, such as TES, HEPES, PIPES, or other buffers, such as sodium bicarbonate. Sample media include, but are not limited to, TALP or HTF. Additional ingredients may include macromolecules such as those discussed herein, for example, albumin, oviductin, gelatin, hylauronic acid, milk, egg yolk, hormones, free radical scavengers (e.g., melanin, vitamin E derivatives, thioredoxine), enzymes (e.g., SOD, catalase), growth factors (e.g., EGF, IGF, PAF, VIP), polymeric molecules (e.g., heparin, dextran, polylysine, PVP or PVA). Additionally, such media may include sperm motility stimulants such as caffeine, follicular fluid, calcium, oxytocin, kallikrien, prostaglandins, thymus extracts, pentoxyfilline, 2-deoxyadenosine, inositol, flavanoids, platelet activating factor, hypotaurine, chondroitin sulfate, and mercaptoethanol. Preferred stimulants are caffeine (e.g., 5 mM) and pentoxyfilline (e.g., 1 mM). Antibiotics and antimycotics may also be included.

In other aspects of this invention, methods are provided for increasing the survival of oocytes, embryos or embryonic stem cells (ESC) in in vitro culture systems. Oocytes, embryos, or ESC are cultured for use in various diagnostic and toxicology assays, in vitro fertilization, or for the propagation of offspring. These methods comprise contacting a sample containing an oocyte, an embryo or ESC with a culture medium that includes a PCAGH.

In general, the medium for extending sperm or culturing sperm, oocytes, embryos or ESC is a balanced salt solution, such as M199, Synthetic Oviduct Fluid, PBS, BO, Test-yolk, Tyrode's, HBSS, Ham's F10, HTF, Menezo's B2, Menezo's B3, Ham's F12, DMEM, TALP, Earle's Buffered Salts, CZB, KSOM, BWW Medium, and emCare Media (PETS, Canton, Tex.). In one embodiment, M199 medium is preferred for culturing oocytes. In certain embodiments, TALP or HTF is preferred for sperm culture medium, and CZB is preferred for embryo culture medium.

The concentration of the PCAGH in the oocyte or embryo medium ranges from 0.001–5% (0.01–5%; 0.05–1%; 0.05–0.5%; 0.1–5%; 0.1–1%). Opt other additives may be present such as amino acids (e.g., glutamic acid) or free radical scavengers. Generally, the additives are a macromolecule, a buffer, an antibiotic and possibly a sperm stimulant if fertilization is to be achieved. As well, a hormone or other protein may be added. Such hormones and proteins include luteinizing hormone, estrogen, progesterone, follicle stimulating hormone, human chorionic gonadotropin, growth factors, follicular fluid and oviductin, albumin and amino acids. Generally, the medium also contains serum from about 1% to 20%. Preferably, serum is from the same animal source as the oocyte or embryo. Sperm, oocytes, or embryos are cultured in the media described above in 5% $CO_2$ and humidified air at 37° C. Cultures may contain a feeder layer comprising somatic cells, generally irradiated cells, cultured cells, or cells with a limited life span in culture (e.g., thymocytes).

VI. Freezing Sperm, Oocytes or Embryos

As noted above, in other aspects of this invention, methods are provided for reducing losses of functional sperm, reducing cellular damage to an oocyte, or reducing cellular damage to an embryo or ESC (embryo stem cell) resulting from storage in a refrigerated, frozen or vitrified state. The methods comprise combining a PCAGH in an amount effective to reduce loss or damage with a sample containing sperm, oocyte, embryo or ESC, and storing the sample in a refrigerated, frozen or vitrified state.

Sperm, oocytes, embryos, and ESC may be obtained in a variety of ways, such as described herein (see Examples). Cryoprotective medium is typically added slowly to the cells in a drop wise fashion. Such medium is prepared by adding an effective concentration of a PCAGH to a simple medium such as Tris buffer or sodium citrate buffer for sperm, PBS for oocytes or embryos, and a balanced culture medium such as M199 for ESC. The PCAGH is generally added at 0.005–30% (e.g., 0.05–20%, 0.05–10%, 0.05–5%, 0.1–10%, 0.1–5%, 1–5%), or for example, at 0.05% for pectin, 0.1% galacturonic acid, 1.0% arabic acid, 5% gum arabic or <5% for arabinogalactan. Alginate is not included.

In addition, a cryoprotective compound is optionally included. Such cryoprotective compounds include permeating and nonpermeating compounds. Most commonly, DMSO, glycerol, propylene glycol, ethylene glycol, or the like are used. Other permeating agents include propanediol, dimethylformamide and acetamide. Nonpermeating agents include polyvinyl alcohol, polyvinyl pyrrolidine, anti-freeze fish or plant proteins, carboxymethylcellulose, serum albumin, hydroxyethyl starch, Ficoll, dextran, gelatin, albumin, egg yolk, milk products, lipid vesicles, or lecithin.

Adjunct compounds that may be added include sugar alcohols, simple sugars (e.g., sucrose, raffinose, trehalose, galactose, and lactose), glycosaminoglycans (e.g., heparin, chrondroitin sulfate), butylated hydroxy toluene, detergents, free-radical scavengers, and anti-oxidants (e.g., vitamin E, taurine), amino acids (e.g., glycine, glutamic acid), and flavanoids and taxol (preferably 0.5–5 $\mu$m). Glycerol is preferred for sperm freezing, and ethylene glycol or DMSO for oocytes, embryos or ESC. Typically, glycerol is added at 3–15%; other suitable concentrations may be readily determined using the methods and assays described herein. Other agents are added typically at a concentration range of approximately 0.1–5%. Proteins, such as human serum albumin, bovine serum albumin, fetal bovine serum, egg yolk, skim milk, gelatin, casein or oviductin, may also be added.

Following suspension of the cells in the cryoprotective medium (e.g., for storage), the container is sealed and subsequently either refrigerated or frozen. Briefly, for refrigeration, the sample is placed in a refrigerator in a container filled with water for one hour or until the temperature reaches 4° C. Samples are then placed in Styrofoam containers with cool packs and may be shipped for insemination, in the case of sperm, the next day. If the sample is to be frozen, the cold sample is aliquoted into cryovials or straws and placed in the vapor phase of liquid nitrogen for one to two hours, and then plunged into the liquid phase of liquid nitrogen for long-term storage or frozen in a programmable computerized freezer. Frozen samples are thawed by warming in a 37° C. water bath and are directly inseminated or washed prior to insemination. Other cooling and freezing protocols may be used. Vitrification involves dehydration of the oocyte or embryos using sugars, Ficoll, or the like. The oocyte or embryo is then added to a cryoprotectant and rapidly moved into liquid nitrogen.

Within the present invention, sperm, oocytes, or embryos may be prepared and stored as described above. Refrigeration is generally an appropriate means for short-term storage, while freezing or vitrification are generally appropriate means for long or short-term storage.

VII. Administration and Uses

The compositions and methods of the present invention increase fertility of animals. These methods are generally applicable to many species, including human, bovine, canine, equine, porcine, ovine, avian, rodent and others. Although useful whenever fertilization is desired, the present invention has particular use in animals and humans that have a fertilization dysfunction in order to increase the likelihood of conception. Such dysfunctions include low sperm count, reduced motility of sperm, and abnormal morphology of sperm. In addition to these dysfunctions, the methods and compositions of the present invention are useful in artificial insemination procedures. Often, in commercial breedings, the male and female are geographically distant requiring the shipment of sperm for insemination. Because of the extended period of time between ejaculation and insemination, shipment in refrigerated or frozen state is necessary. As well, for particularly valuable or rare animals, long-term storage may be desirable. For humans, geographical distance or time considerations may necessitate storage of sperm. Men with diseases where radiation treatment is part of therapy or prior to vasectomies may desire to have sperm stored for future use. After frozen storage, cells are often cultured during end use. Survival and health of the cells in culture have been shown to be improved by addition of a PCAGH to the cryopreservative medium.

The lubricant is useful for all situations involving sperm collection, coitus, and artificial insemination. Currently, sperm collection is done without any lubrication because of the spermicidal nature of commercial lubricants and saliva (Goldenberg et al., *Fertility and Sterility* 26:872–723, 1975, Scoeman & Tyler, *J. Reprod. Fert.* 2:275–281, 1985, Miller et al., *Fert. and Steril.* 61:1171–1173, 1994). The use of a non-spermicidal lubricant containing a compound that improves sperm function and increases potential fertility is desirable for the comfort of the donor. As such, the lubricant may be applied to condoms or other collection devices, such as catheters or vials. Infertile couples often have the need for lubricants due to the stress of timed coitus and difficulty in conception. However, because lubricants are spermicidal, they are not recommended for use. In these cases, the application of a lubricant intravaginally, with or without an applicator, would be desirable and beneficial because sperm function would be increased (FIG. 1). Similarly, the lubricant may be applied intravaginally prior to artificial insemination to improve the chances of conception. In either case, normal sperm should swim into the cervical mucus within three minutes of coitus, with a maximum number found in the cervix three hours post-coitus. The acidic environment of the vagina inactivates sperm left in the vagina over a four-hour time period. Intravaginal application of the lubricant product improves sperm survival in the vagina and increases cervical mucus penetration.

The following examples are offered by way of illustration, and not by way of limitation.

EXAMPLES

Example 1

Media for Sperm Isolations and Culture

Sperm function assays such as sperm motility, viability and functional membrane health (HOS) are used to determine and/or compare the biological activity of a PCAGH. Sperm samples from a male donor are obtained either from a fresh ejaculate of raw semen or a refrigerated or frozen sample processed by washing or extending as described herein. Basal medium is used throughout as follows: glucose-free TALP (Table 1) is prepared for bovine sperm, TALP supplemented with glucose (5 mM glucose) is prepared for other animal species, and human tubal fluid (HTF) from a powder mix or from a recipe (Table 2) is prepared for separation of human sperm. To the base medium, PCAGH is added, such as 0.05% pectin, 0.1% galacturonic acid, 0.5% arabic acid or 0.05% gum arabic. The medium is then filtered through a 0.2$\mu$ filter.

TABLE 1

| GLUCOSE FREE TALP | |
|---|---|
| Ingredient | g/500 ml |
| NaCl | 2.922 |
| KCl | 0.1156 |
| NaHCO$_3$ | 1.0500 |
| NaH$_2$PO$_4$H$_2$O | 0.0200 |
| Na Lactate (60% syrup) | 1841 $\mu$l |
| CaCl$_2$·2H$_2$O | 0.1546 |
| MgCl·6H$_2$O | 0.0407 |
| Phenol Red | 0.0050 |
| HEPES | 1.1915 |
| BSA Fraction V | 3.0 |
| Gentimycin Sulfate | 500 $\mu$l |
| Na Pyruvate | 25 ml |

Adjust pH to 7.2, filter (0.2 $\mu$; pH will adjust up to 7.4) and store at 5° C.

TABLE 2

MODIFIED HUMAN TUBAL FLUID

| Ingredient | mM |
| --- | --- |
| NaCl | 97.6 |
| KCl | 4.7 |
| MgSO$_4$·7H$_2$O | 0.2 |
| Na lactate | 21.4 |
| Na pyruvate | 0.33 |
| NaHCO$_3$ | 25.0 |
| CaCl$_2$·2H$_2$O | 2.04 |
| Glutamine | 1.0 |
| EDTA | 0.1 |

Adjust pH to 7.2, filter (0.2 μ; pH will adjust up to 7.4) and store at 5° C.

Example 2

Sperm Functional Assays

Sperm Count in a Suspension. Sperm cells are suspended in culture medium or a freezing medium. Numbers in a suspension are counted either manually using a hemocytometer or Makler, or by an automated Coulter counter system, a spectrophotometer, or a computer assisted semen analyzer (CASA). For example, 6 μl of sperm suspension are placed on a Makler chamber (Fertility Technologies, Natick, Mass.). The number of sperm counted in 10 squares is equivalent to the number of sperm/ml in the original suspension. Appropriate dilutions are made so that at least 100 sperm are counted.

Sperm Morphology. Sperm morphology or shape is determined by smearing a 10 μl aliquot of sperm sample at approximately 25×10$^6$ cells/ml onto a slide and staining with a differential stain such as Wright Giemsa at 0.1% (w/v), for 30 minutes. Sperm are then observed under a microscope and categorized as to normal or abnormal shapes (morphology); (Kruger et al., *Urology* 30:248, 1987); or by CASA sorting into normal or abnormal shapes based on computerized image analysis (Davis, *Infertility & Reproductive Medicine Clinics* 3:341, 1992).

Sperm Motility. Sperm motility measurements may be performed by subjective visual determination using a phase contrast microscope to group sperm into total percent motile (swimming), and total percent progressively motile (swimming forward). Also the speed of those sperm which are progressively motile is determined, i.e., fast, medium, slow.

Alternatively, CASA can be used to objectively determine the motility characteristics of individual sperm cells in a sample (Davis, *Infertility & Reproductive Medicine Clinics* 3:341, 1992). A 7 μl sperm sample is placed onto a slide or chamber designed for CASA, and the computer tracks individual sperm cells and determines their motility as to speed over distance. Data is then expressed as percent motile, and specific measurements are given for parameters, such as mean path velocity and track speed. The measurements of velocity and linearity correlate with future fertility in several species studied.

Sperm Viability. Sperm viability, or the percent of live sperm in a sample, is determined by membrane exclusion stains, such as Hoechst stain 33258 or eosin-nigrosin. Dead sperm stain positive because the membranes are disrupted, allowing the stain to penetrate the cells. For example, 10 μl of eosin nigrosin stain (American College of Theriogenologists, Hastings, Nebr.) is mixed with 10 μl of sperm sample. This mixture is then smeared across the slide and the number of pink (dead) and white (live) sperm are determined. Viability is expressed as the number of live cells divided by the total number of live and dead cells.

ATP levels in a sperm sample may also be utilized to determine viability. These are measured using a simple luminometer and a firefly enzyme which fluoresces when in contact with active ATP from living sperm cells (Sperm Viability Test by Firezyme, Nova Scotia, Canada). Comparing the amount of fluorescence to a standard curve allows one to determine the number of live sperm present in sample.

Membrane Function of Sperm. Functional membrane health of a sperm cell, determined by the hypo-osmotic swell test (HOS), involves putting sperm into a solution with too few salts (hypo-osmotic). This triggers sperm with healthy membranes to pump salt out of the cell and causes the membranes of the sperm to shrink as the cell grows smaller. The sperm tail then curls inside this tighter membrane. Sperm with a curled tail are the sperm which are healthy and have functional membranes. A hypo-osmotic solution of 75 mmol/L fructose and 25 mmol/L sodium citrate is prepared. One ml of this solution is added to 100 μl of sperm sample. After incubation for 30 minutes, a 10 μl aliquot of the mixture is placed on a slide and the percentage of sperm with curled tails is determined out of 100 sperm evaluated (Jeyendran et al., *J. Reprod. Fert.* 70:219, 1984).

Lipid Membrane Peroxidation of Sperm. Damage to the sperm membrane by reactive oxygen species can also be determined by measuring lipid membrane peroxidation. Sperm are incubated in 0.63% ferrous sulfate and 0.23% ascorbic acid for one hour in a 37° C. water bath. Proteins are precipitated with ice-cold 40% trichloroacetic acid. The supernatant is collected by centrifugation at 3500×g for 25 min. in the cold and reacted by boiling for 10 min. with 2% thiobarbituric acid in 0.05N NaOH. The resultant malondialdehyde (MDA) formation is quantified by measuring absorbance at 534 nm as compared to an MDA standard. Lipid peroxidation is expressed as nM MDA/10s sperm. Frozen, thawed sperm have increased rates of LPO as compared to freshly ejaculated sperm. (Bell et al., *J. Andrology* 14:472–478, 1993). However, freezing sperm in a PCAGH-containing medium decreases the lipid peroxidation as compared to existing methods.

Zona Binding Assay. The ability of sperm to undergo capacitation (a biochemical change in sperm which must occur prior to fertilization), and bind to an oocyte can be measured using a zona binding assay (Franken et al., *Fert. Ster.* 59:1075, 1993). In this test live, normal sperm are incubated under conditions which trigger capacitation. Bull sperm are incubated with 10 IU/ml of heparin in TALP for 4 hours. Sperm are then incubated for 1 hour with dead oocytes, which are surrounded by the acellular coating called the zona pellucida. Capacitated sperm bind to the zona and the number binding are counted under the microscope. This number correlates with the number of normal capacitated sperm in a sample and with fertility of a sperm sample.

Sperm Penetration Assay. This test is conducted to determine the ability of sperm to penetrate into the oocyte (Rogers et al., *Fert. Ster.* 32:664, 1979). Zona-free hamster oocytes are used to perform this test for sperm of any species. Capacitated sperm ($1 \times 10^5$ sperm in 100 µl of BWW medium) are incubated with the hamster oocytes for 3 hours. The oocytes are then stained (with 1% aceto-lacmoid) and the number of sperm penetrating each one is counted.

Sperm Survival in Culture. Survival in culture is determined by placing an aliquot of $1 \times 10^6$ sperm in 2 cm² wells with 500 µl of TALP or HTF medium in an incubator at 37° C. in 5% $CO_2$ and air. At timed intervals (e.g. every 8 hours), the percentage of motile sperm in the well are determined visually using an inverted microscope. Also, the forward speed is determined (fast, medium, slow). A sample is determined to be no longer viable when less than 5% of the sperm have progressive motility.

Figure 2:
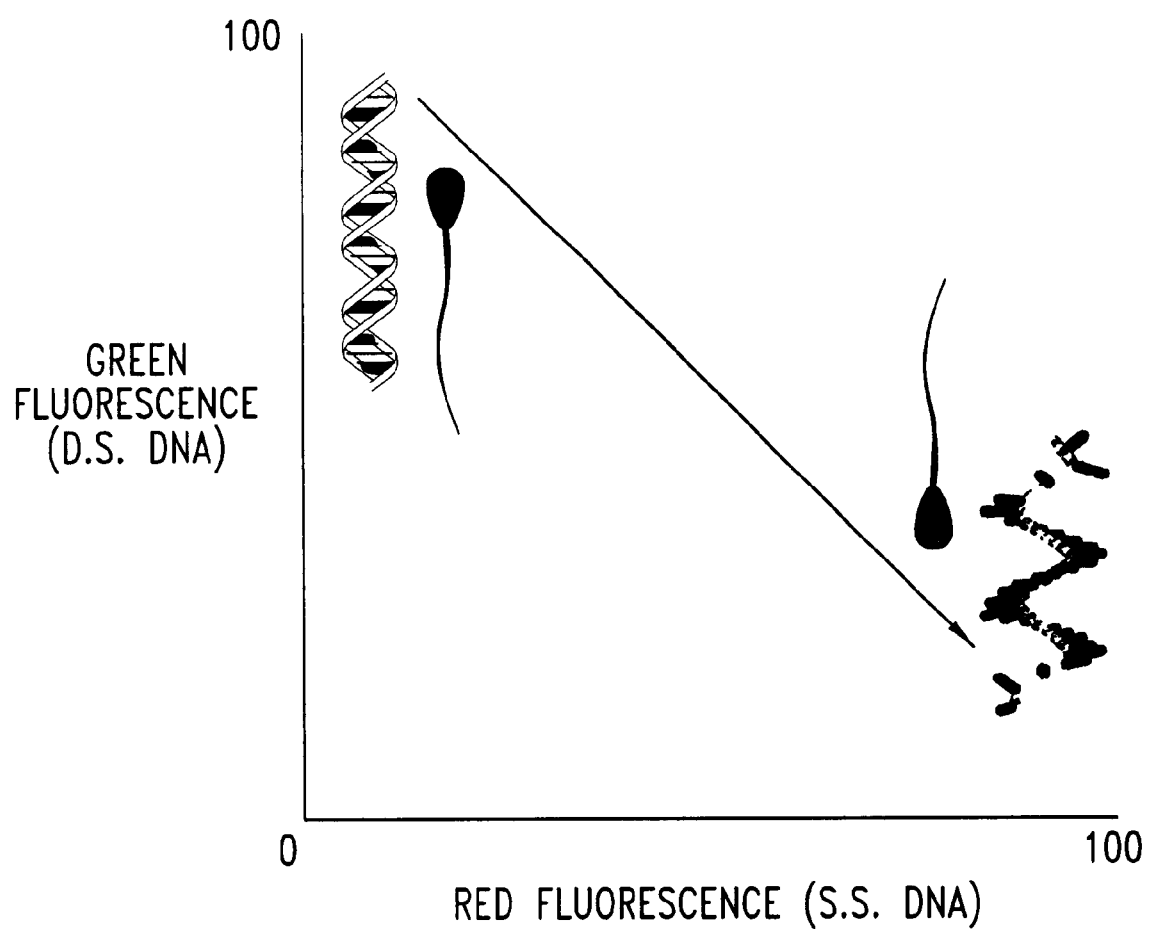
FIG. 2 is a graph illustrating the shift of fluorescence output following DNA damage.

Sperm Chromatin Sensitivity Assay. This assay is based on the metachromatic staining of single and double stranded DNA by acridine orange stain, following excitation with 488 nm light, green fluorescence comes from double strand DNA and red from single strand (FIG. 2). The extent of DNA denaturation in a sample is seen as alpha=red/red+green as evaluated by the mean of alpha, the SD of alpha and the coefficient of variation for alpha. In all cases sperm to be studied are mixed with a TNE buffer (0.01 mol/L Trisaminomethane-HCI, 0.15 NaCI, and 1 mM EDTA) and flash frozen. Sperm samples are then subjected to 0.1% Triton-X, 0.08N HCI, 0.15 NaCI. This induces partial denaturation of DNA in sperm with abnormal chromatin. Sperm are then stained with 6 µg/ml acridine orange and run through a flow cytometer to determine the α value.

Sperm Function in the Female. The ability of sperm to survive and function in the female can be determined by the percent of oocytes that are fertilized in a superovulated female (unusually large numbers of oocytes ovulated due to hormonal stimulation with follicle stimulating hormone). Oocytes are retrieved from the oviduct soon after fertilization by the sperm (at approximately 24 hours). Fertilization is assessed by staining with 1% aceto-orcein. Alternatively, embryos resulting from fertilized oocytes are retrieved from the uterus several days after fertilization and counted. The ability of sperm to survive and function in the female is also determined by the numbers of accessory sperm bound to an oocyte recovered from the oviduct or uterus. The number of sperm able to reach an oocyte and bind to it, even if they are not involved in fertilization itself, is highly correlated to sperm fertility from a sample (Dejarnette et al., *J. Am. Sci.* 70:484, 1992).

In Vitro Fertilization. In vitro fertilization rates are determined by maturing oocytes in vitro in M199 media with 50 µg luteinizing hormone/ml (Brackett and Zuelke, *Theriogenology* 39:43, 1993). Following incubation, sperm are capacitated with heparin (bull sperm) or by an 18 hour incubation with albumin containing medium (human sperm) and incubated with oocytes for 24 hr. Oocytes are then stained with a 1% aceto-orcein stain to determine the percent fertilized, or left in culture to divide and the number of forming embryos are counted.

Cervical Mucus Penetration of Sperm. The ability of sperm to penetrate reproductive tract mucus of the female is measured in vitro by exposing sperm to a track containing cervical mucus (Tru-Trax, Fertility Technologies, Natick, Mass.) and measuring the distance the sperm have penetrated through the mucus at time specific intervals. An in vivo post coital test involves recovery of cervical mucus from the female with a speculum at 3–6 hrs post coitally. The number of sperm with good motility per high power field should be >10 if sperm function and cervical mucus are normal.

Example 3

Methods to Determine Sperm Function

Figure 3:
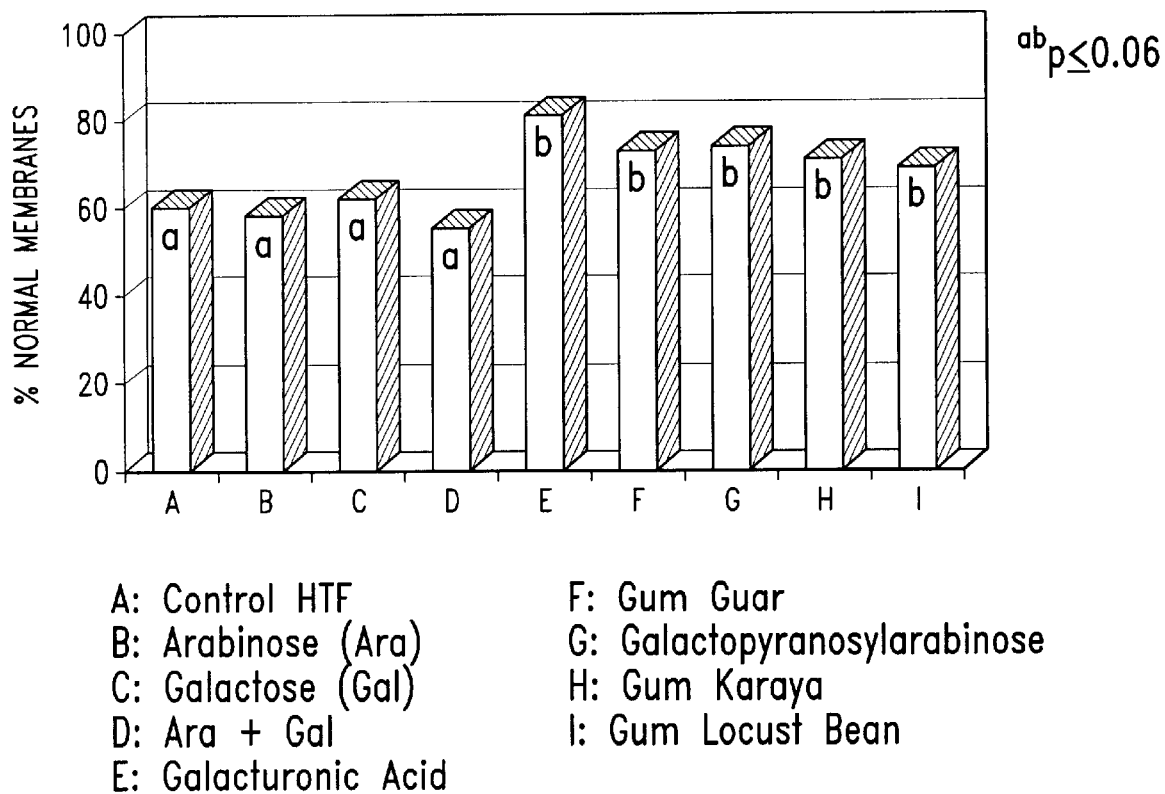
FIG. 3 is a chart showing the percentage of sperm with normal membranes after culture for 24 hours in HTF alone or containing various carbohydrates, including PCAGHs.
Figure 4:
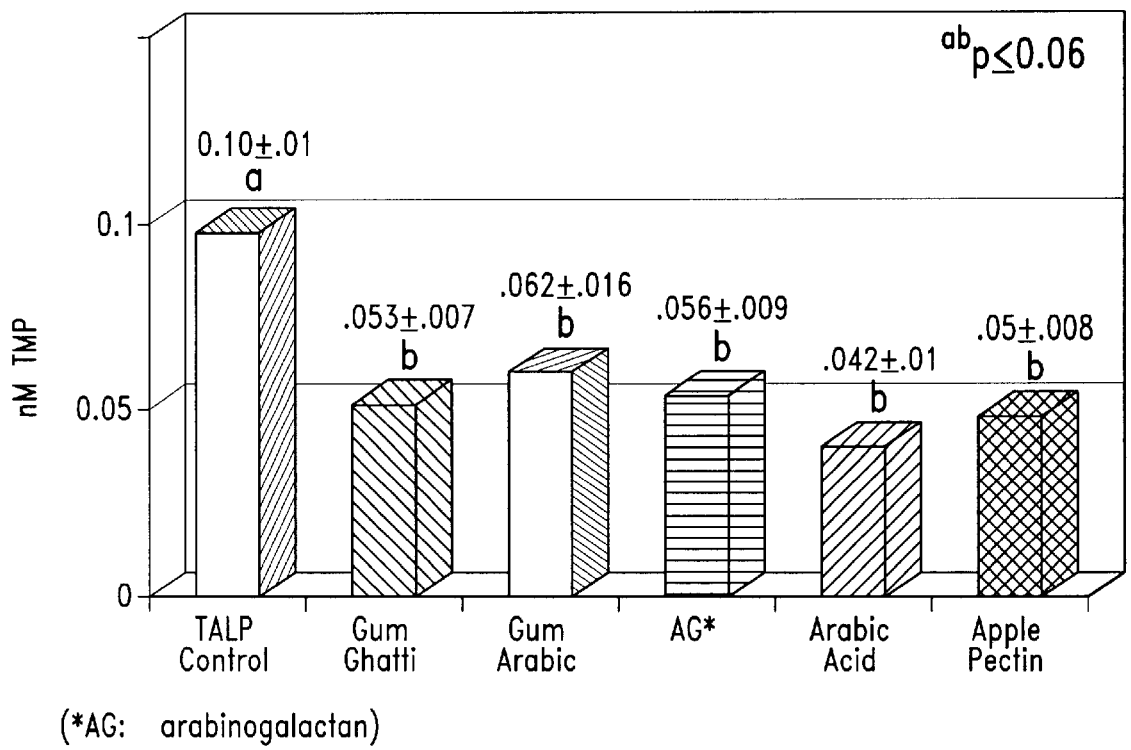
FIG. 4 is a chart illustrating lipid membrane peroxidation levels of bull sperm cultured for 4 hours with various PCAGH.

Samples containing sperm are incubated at 37° C. (human) or 39° C. (animal) in 5% $CO_2$ and humidified air. At various timed intervals, sperm survival rate, motility characteristics, functional membrane health and membrane lipid peroxidation levels are determined as described in Example 2. Sperm cultured with a variety of PCAGHs (galacturonic acid, gum guar, galactopyranosylarabinose, gum karaya and gum locust bean) show superior sperm motility throughout a 24-hr culture period compared to sperm cultured in the monomeric sugar units of arabinose and galactose or in control medium with no polysaccharides (Table 3). In this same example, sperm show superior functional membrane health as determined by HOS testing (FIG. 3) and reduced levels of membrane lipid peroxidation (FIG. 4). Furthermore, sperm cultured in pectin, gum ghatti, gum arabic, arabic acid, and arabinogalactan show superior sperm motility characteristics of percent motility and forward speed over a 24-hr culture period, at the concentrations chosen, compared to sperm cultured in the PCAGH carageenan and fucoidan or in control medium without polysaccharides (Table 4).

TABLE 3

HUMAN SPERM CULTURED IN A VARIETY OF PCAGH OR THE MONOMERIC UNITS OF ARABINOSE, GALACTOSE OR GALACTURONIC ACID

| Culture | Treatments | | | | | | | | |
|---|---|---|---|---|---|---|---|---|---|
| Time | 1 | 2 | 3 | 4 | 5 | 6 | 7 | 8 | 9 |
| 3 hr | = | = | = | + | + | + | ± | ± | c |
| 15 hr | = | = | = | + | + | + | + | + | c |
| 24 hr | = | = | = | + | + | + | + | + | c |

(+): Superior sperm motility compared to control HTF
(=): Equivalent sperm motility compared to control HTF
(−): Inferior sperm motility compared to control HTF
Treatments:
1. arabinose
2. galactose
3. arabinose + galactose
4. galacturonic acid
5. gum guar
6. galactopyranosylarabinose
7. gum karaya
8. gum locust bean
9. control HTF

TABLE 4

NUMBER OF TIMES EACH TREATMENT SCORED AS ONE OF THE TOP THREE TREATMENTS BASED ON SPERM MOTILITY CHARACTERISTICS

|  | Pectin@ | gum ghatti | cara- geenan^ | gum arabic | fucoidan^ | arabino galactan | arabic acid | control TALP |
|---|---|---|---|---|---|---|---|---|
| 3 hr* | 9+ | 6 | 0 | 6 | 0 | 5 | 6 | 2 |
| 6 hr* | 10 | 5 | 2 | 7 | 0 | 4 | 4 | 1 |
| 10 hr** | 6 | 2 | 1 | 5 | 0 | 4 | 3 | 2 |
| 24 hr* | 9 | 3 | 2 | 6 | 0 | 4 | 4 | 2 |

@polysaccharides added at 0.05%
*11 replicates
**7 replicates
+Number of times each treatment scored as one of the top three treatments over eleven replicates based on sperm motility characteristics of % motile and forward speed over 24 hours of culture showing benefit of PCAGH over medium control.
^PCAGHs that are highly sulfated.

Example 4

Enzymatic and Chemical Fractionation of Pectin and Gum Arabic

Figure 5:
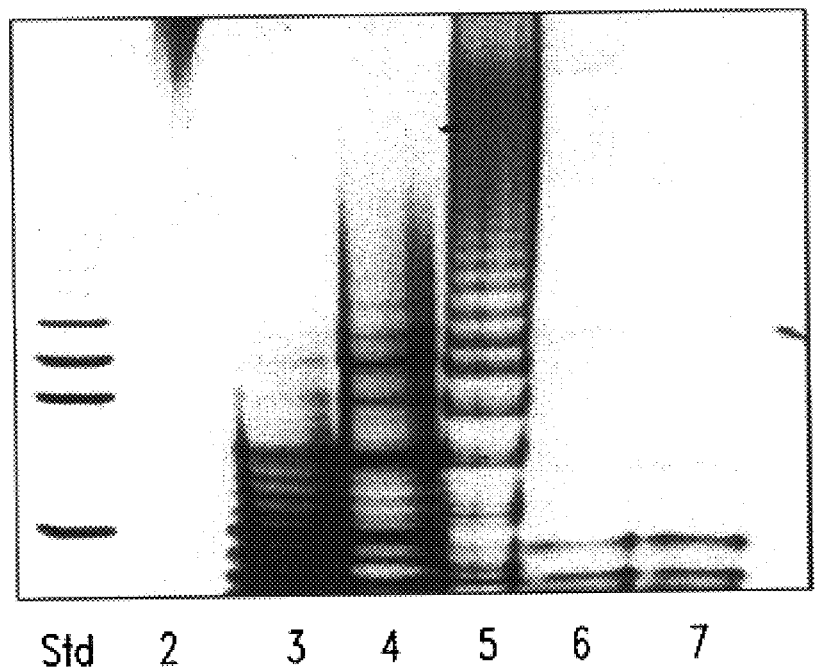
FIG. 5 is a stained electrophoretic gel of apple pectin following various enzymatic treatments.

Fractionation of Pectin by Enzymatic Digestion. 80 μg of pectin (Sigma Chemical Co., St. Louis, Mo.) are digested with endo-arabinanase from Aspergillus niger, α-L-arabinofuranosidase from A. niger, and endo-polygalacturonanase from A. niger (Megazyme, Bozeman, Mont.). Samples are incubated overnight at 45° C., boiled to inactivate enzyme and fractionated using Centricon 30 microconcentrators (Amicon) into a>30,000 MW and a<30,000 MW fraction. The endo-galacturonanase cleaves the polygalacturonic acid backbone yielding a variety of different MW polymers which include side chains. α-L-arabinofuranosidase cleaves arabinofuranosyl units from the reducing end of the side chains while endo-arabinanase removes the side chains from the polygalacturonic backbone. Gel fractionation of the digests shows the different size/polymer length of the oligomers following enzymatic digestion (FIG. 5).

Enzymatic fractions are dried using a Speed Vac concentrator, washed in distilled water and redried. Fractions are resuspended in HTF to 0.05% (for pectin). Cultured sperm are incubated at 37° C. in 5% $CO_2$ and humidified air. At various timed intervals, sperm motility characteristics are determined as described in Example 2. Enzymatic fractions greater than 30,000 MW of the endo-polygalacturonanase and endo-arabinanase, as well as the >30,000 MW of undigested pectin, stimulate superior sperm motility (both percentage of motile sperm and velocity) compared to control HTF (Table 5). Culture of sperm in fractions representing all digested fragments <30K resulted in equivocal or inferior sperm motility. Enzymatic derivatives of pectin therefore elicit different biological responses with respect to improving sperm motility during culture.

TABLE 5

SPERM MOTILITY IN PECTIN FRACTIONS

| Culture Time | Treatments | | | | | | | | |
|---|---|---|---|---|---|---|---|---|---|
|  | 1 | 2 | 3 | 4 | 5 | 6 | 7 | 8 | 9 |
| 3 hrs | + | = | = | = | + | + | − | − | c |
| 17 hrs | + | ± | = | = | + | + | − | − | c |
| 24 hrs | + | = | = | = | + | + | − | − | c |

(+): Superior sperm motility compared to control HTF
(=): Equivalent sperm motility compared to control HTF
(−): Inferior sperm motility compared to control HTF
Treatments
1: endo-polygalacturonanase, >30 K
2: endo-arabinanase, >30 K
3: undigested pectin, <30 K
4: endo-polygalacturonanase, <30 K
5: α-L-arabinofuranosidase, >30 K
6: undigested pectin, >30 K
7: α-L-arabinofuranosidase, <30 K
8: endo-arabinanase, <30 K
9: Control HTF Chemical Fractionation of Pectin and Gum Arabic. Powdered commercial pectin and gum arabic (2 g; Sigma Chemical Co., St. Louis, Mo.) are suspended in 100 ml 96% ethanol and heated to 70° C. for 30 min. Alcohol soluble and insoluble fractions are then separated by centrifugation (3100×g for 15 min). The procedure is repeated three times. Alcohol insoluble fractions are air dried at room temperature overnight and extracted with dilute hydrochloric acid (0.1 M HCl, 80° C., 5 hr). Acid insoluble and soluble fractions are separated by centrifugation. The acid insoluble fraction is washed in distilled water, centrifuged and dried. A sample is taken and suspended in sperm culture to an approximate concentration of 0.05% for sperm analysis. The acid soluble fraction is dialyzed against distilled water overnight and a fraction (20 μl or 200 μl) diluted in 10 ml sperm culture medium for sperm analysis.

Sperm cultured in the above fractions are incubated at 37° C. in 5% $CO_2$ and humidified air. At various timed intervals, sperm survival rate, motility characteristics and functional membrane health are determined as described herein. Sperm cultured in the acid soluble fraction of acid hydrolyzed pectin and gum arabic show equivalent or superior function (as measured by sperm survival over 24 hours, sperm motility characteristics and HOS) compared to the undigested pectin and gum arabic (Table 6). The acid soluble fractions would contain small MW oligomers of the PCAGHs as well as monomeric galacturonic acid units.

TABLE 6

SPERM FUNCTION IN FRACTIONS OF PECTIN AND GUM ARABIC (N = 4 HUMAN EJACULATES)

| Fractions Evaluated | Scores* |
|---|---|
| Acid Soluble Fractions: | |
| Pectin (20 µl/10 ml HTF) | 5/9 |
| Pectin (200 µl/10 ml HTF) | 7/9 |
| Gum Arabic (20 µl/10 ml HTF) | 7/9 |
| Gum Arabic (200 µl/10 ml HTF) | 8/9 |
| Undigested Pectin (0.05%) | 8/9 |
| Undigested Gum Arabic (0.05%) | 7/9 |

*Data expressed as # of times out of a possible total of nine that a fraction scored better than control HTF medium. Other fractions not shown had overall scores <5/9 (total fractions evaluated = 15).

Molecular Weight Fractionation of Undigested Pectin. Powdered pectin is diluted in sperm culture medium to 0.05% and fractionated into the following MW categories by filtration centrifugation: >0.2µ, >100 kDa and <0.2µ, and <100 kD. Each fraction obtained is resuspended to the final original volume in culture medium to approximate the percentage of the fraction in the original sample.

Figure 6:
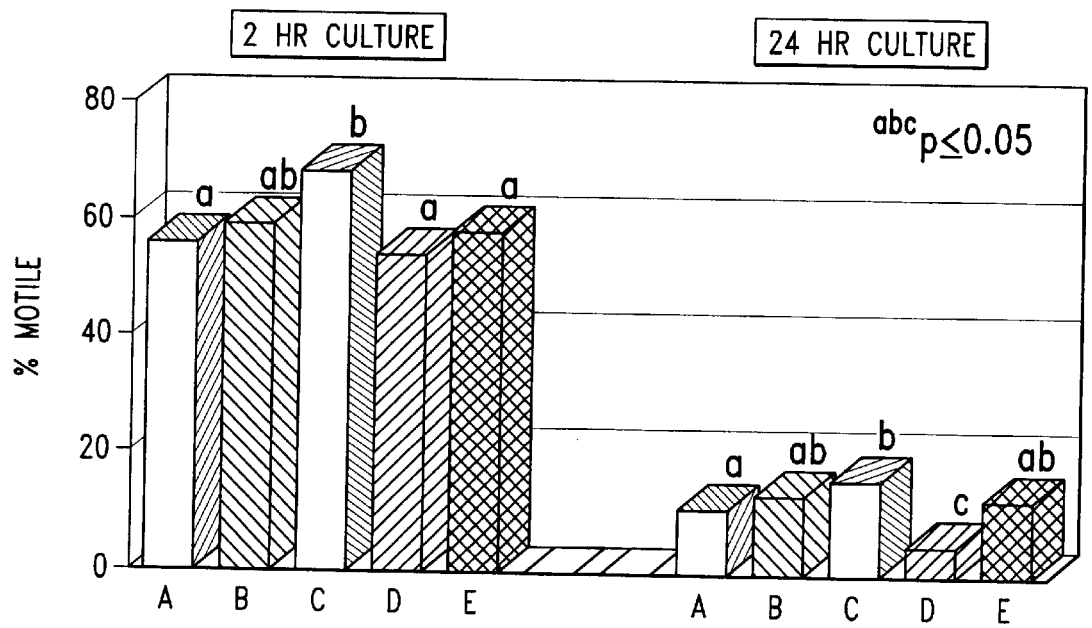
FIG. 6 is a chart showing the percentage of bull sperm that are motile following a 2 or 24 hour culture in TALP containing various fractions of pectin.

Sperm cultured in the above fractions are incubated at 37° C. in 5% $CO_2$ and humidified air. At various timed intervals, sperm survival rate and motility are determined as described in Example 2. Bull sperm cultured with pectin fractions less than 100 kDa demonstrate superior motility characteristics compared to sperm cultured in media which contains pectin fractions greater than this MW (FIG. 6). Sperm motility characteristics of sperm cultured with pectin fractions >100 kDa but less than 0.2µ w demonstrate inferior motility characteristics, particularly at 24 hr.

Example 5

Method of Sperm Washing

Sperm samples from a male donor are obtained either from a fresh ejaculate in raw semen or a refrigerated or frozen sample processed by washing or extending as described herein. Basal medium is used throughout as follows: glucose-free TALP (Table 1) is prepared for separation of bovine sperm, TALP supplemented with glucose (5 mM glucose) is prepared for separation of other animal sperm, and human tubal fluid (HTF) from a powder mix or from a recipe (Table 2) is prepared for separation of human sperm. Gum arabic is added to a final concentration of 20% and gelatin is added to a final concentration of 1.0%, alternately human serum albumin at 5 mg/ml can be used as the protein macromolecule.

For each species, sperm are washed by aliquoting into a centrifuge tube a volume of medium that is 1–2 times the volume of an ejaculate (i.e., 3–6 ml medium for a 3 ml human ejaculate). The sample is then centrifuged at 300×g for 15 min or its centrifugal equivalent. The supernatant is aspirated off. The pellet of sperm is then resuspended with the medium of choice (depending on desired use), such as a freezing or insemination extender, or a culture medium for performing sperm functional assays as in Example 2.

Figure 7A:
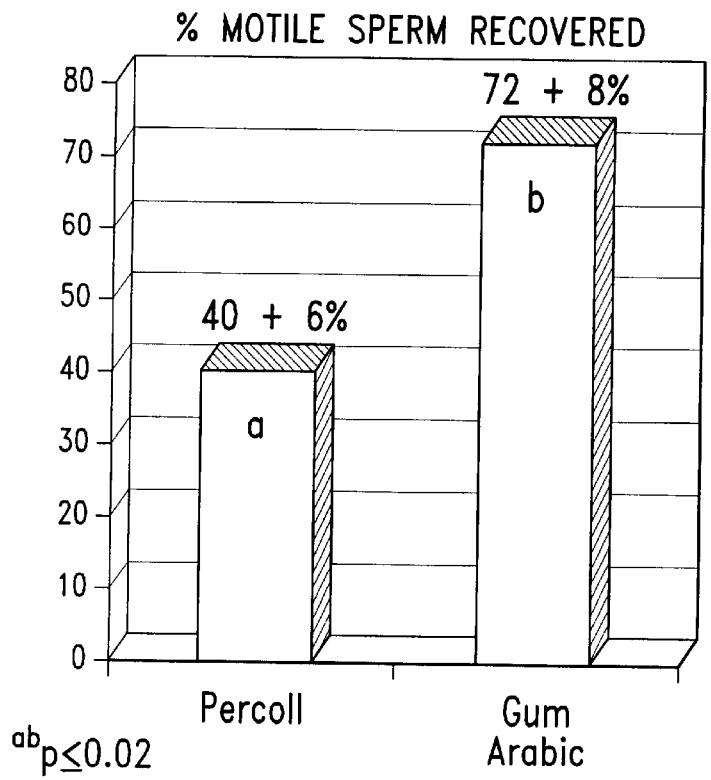
FIG. 7 is a pair of charts demonstrating the percentage of motile sperm (A) and sperm with normal membranes (B) after washing sperm through Percoll or a buffer containing gum arabic. Semen from four ejaculates were tested.
Figure 7B:
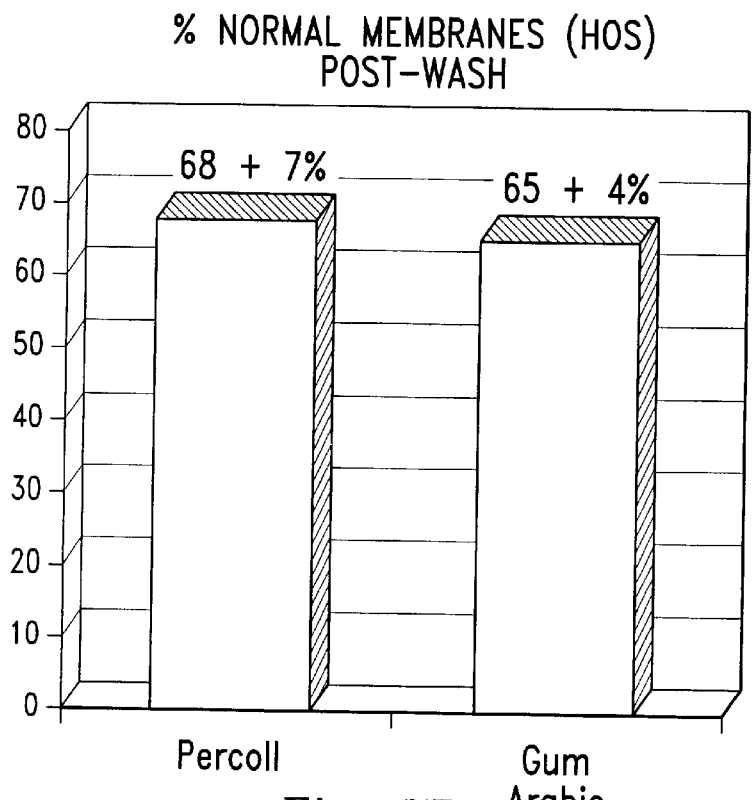

The gum arabic gradient results in recovery of more of the motile sperm from the ejaculate. (FIG. 7) These sperm have superior membrane function, and subsequently live longer in culture than do sperm recovered from a Percoll gradient (Table 6).

TABLE 6

MEAN SURVIVAL IN CULTURE OF BULL SPERM AFTER SEPARATION

| Percoll Control | 24 ± 4 hours |
|---|---|
| Gradient | 32 ± 6 hours |

A continuous gradient of sperm wash product is prepared using a balanced salt medium. Glucose-free TALP is used for a bovine sperm, a glucose containing TALP for other animal species, and HTF for human sperm. A macromolecule such as human serum albumin or gelatin is added to the medium at approximately 0.5%, as is a PCAGH such as gum arabic at 20%. The concentration of macromolecule(s) and PCAGHs can be altered to accommodate the density of sperm from each species. The mixture is filtered through a 0.45 micron filter into a centrifuge tube. A semen sample is placed over the wash product at a ratio of 1 part semen to 2 parts wash product. The sample is then washed through the PCAGH product by centrifugation at 300×g for 15 min. The pellet of sperm is assayed in terms of sperm numbers recovered, morphology of recovered sperm, sperm motility, membrane function, survival time in culture and IVF rates.

An additional advantage of using PCAGH is that a follow-up wash step to remove them is not required since they are nontoxic to sperm, as is not the case of Percoll which requires a wash step. Additionally, a slight antimicrobial activity for the PCAGH is seen which could add further benefit to the washing of semen samples (Table 7).

TABLE 7

POTENTIAL ANTIMICROBIAL ACTIVITY OF PCAGH

| | Staphylococcus | Streptococcus | Haemophilus |
|---|---|---|---|
| Arabinogalactan | xx | xx | xx |
| Pectin | | xx | | xx: Zone of inhibition on a Mueller Hinton plate as demonstrated for this specific PCAGH-organism combination.

Example 6

Sperm Freezing or Refrigeration Technique

Sperm samples are obtained as fresh ejaculates. Sperm are either washed through a PCAGH containing gradient (as above) or are left in raw semen. Freezing medium is prepared using a Tris-buffered solution containing TES, Tris, sodium citrate, fructose, penicillin, streptomycin (Prins and Weidel, Fert. Ster. 46:147, 1986). To this solution, 20% egg yolk, 7% glycerol, and an effective amount of a PCAGH, such as 0.1% gum guar, 0.05% pectin, 1% arabinogalactan or 0.1% galacturonic acid is added. Additionally, 1 µM taxol or 0.25% methylcellulose may be added to the freeze mixture. Egg yolk free recipes may also be used (Table 8). The medium is then filtered through a 0.45µ filter. The freezing medium is added drop by drop to the raw semen until a one to one dilution has been reached. The extended sperm sample is then placed in a refrigerator until the mixture reaches 4° C. The sperm mix is aliquoted into freezing straws or cryovials, placed in liquid nitrogen vapor phase for 1 hour, and then plunged into liquid nitrogen. If chilled, sperm samples are shipped in Styrofoam containers at this time with Kool packs and mailed overnight for insemination the next day. If frozen in lN$_2$, sperm samples are placed in the vapor phase of lN2 and can be mailed for next day delivery or stored.

Sperm refrigerated or frozen with PCAGH extender is assayed for function after storage by thawing the sperm sample in a 37° C. water bath and evaluating motility, viability, zona binding, membrane function, lipid peroxidation, sperm chromatin, IVF, and sperm function in the female.

Figure 8:
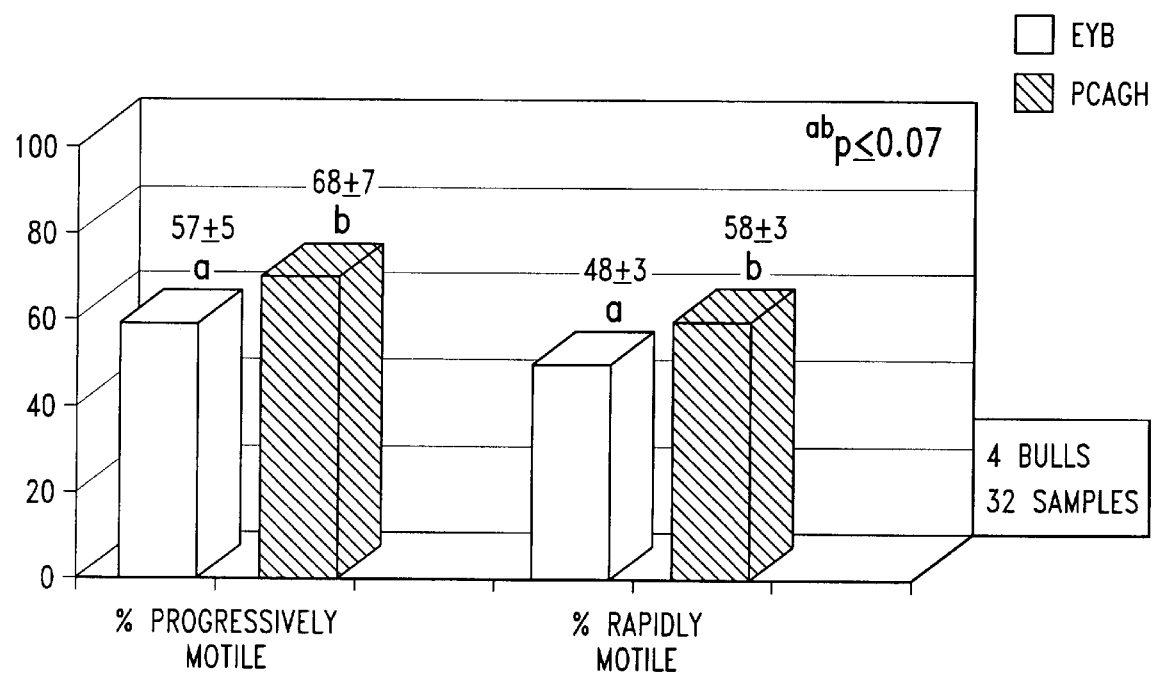
FIG. 8 is a chart demonstrating the motility characteristics of bull sperm frozen in egg yolk buffer (EYB) extender or PCAGH extender.
Figure 9:
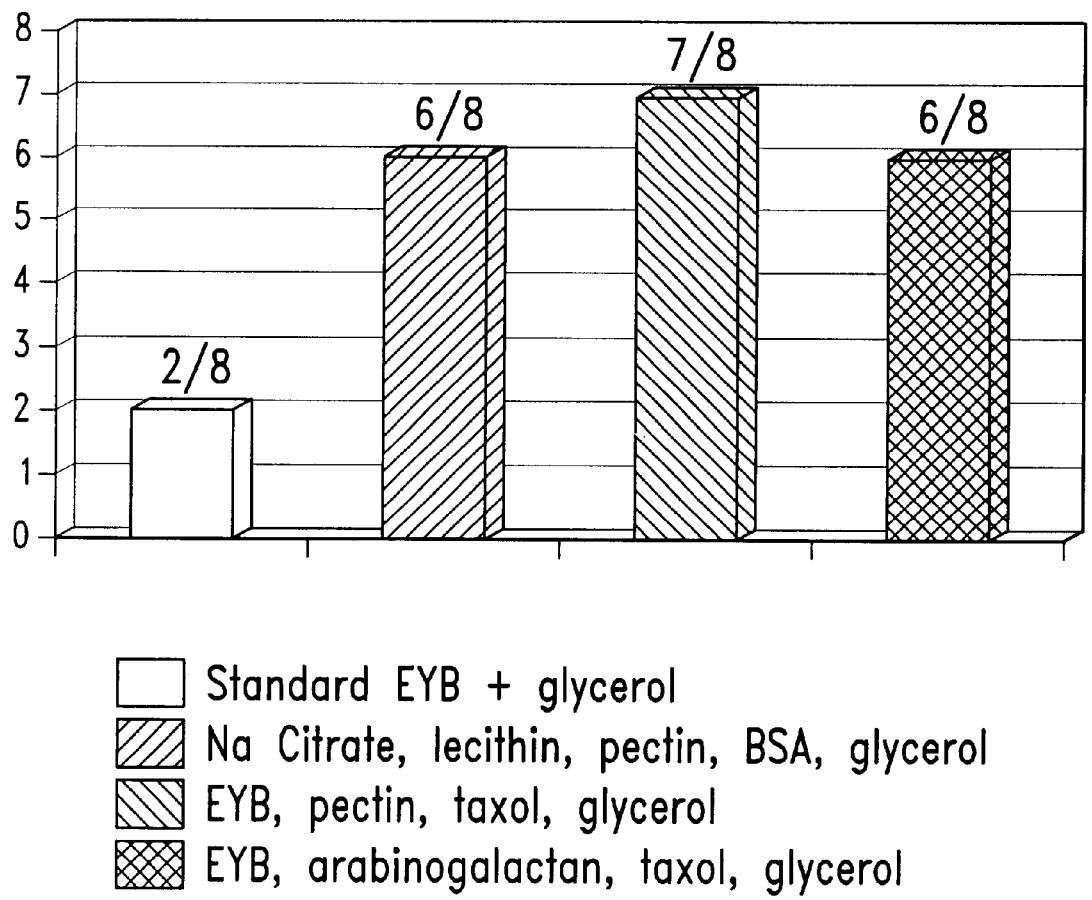
FIG. 9 is a chart showing the number of bull sperm samples having >5% motility after freezing and thawing in the shown extenders, followed by 24 hours of culture.
Figure 10:
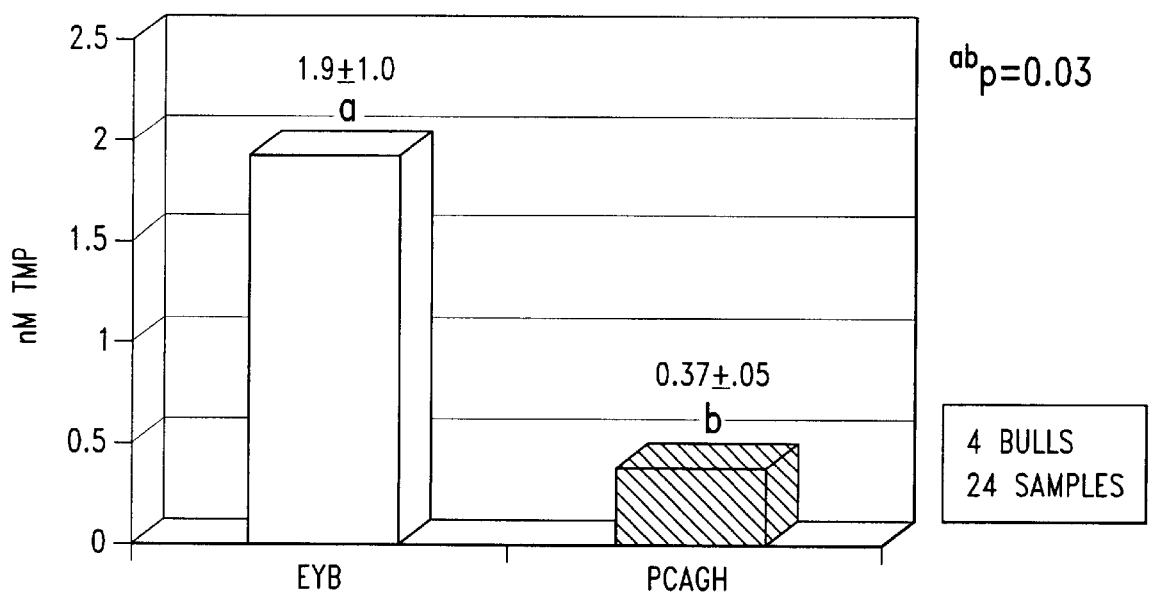
FIG. 10 is a chart showing the extent of lipid membrane peroxidation for frozen bull sperm after holding sperm for 10 minutes after thawing in egg yolk buffer (EYB) extender or PCAGH extender.
Figure 11A:
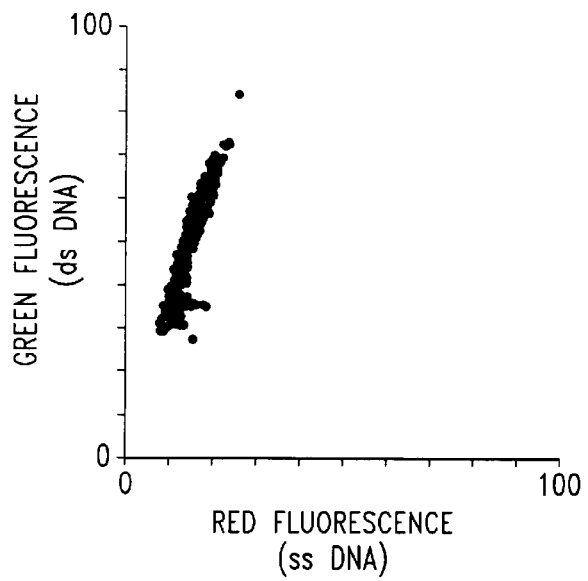
FIGS. 11A–11D are flow cytometry profiles of DNA from sperm frozen with PCAGH (A) and (B) or egg yolk buffer (C) and (D) extenders.
Figure 11B:
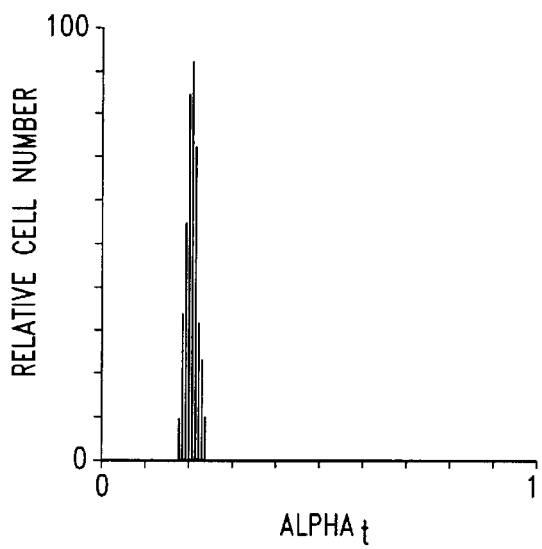
Figure 11C:
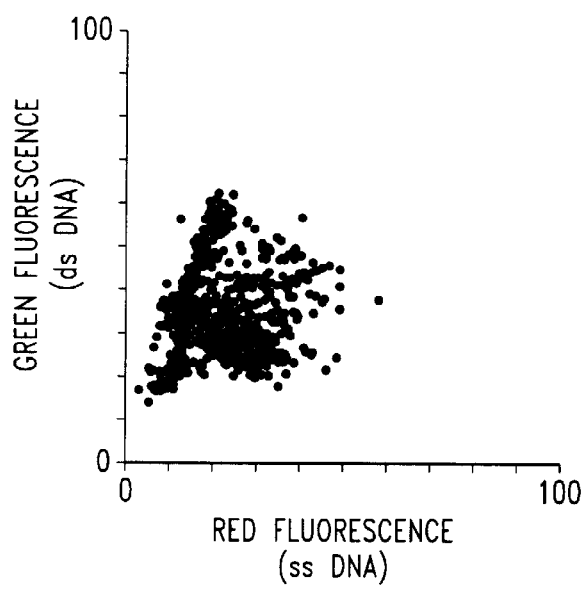
Figure 11D:
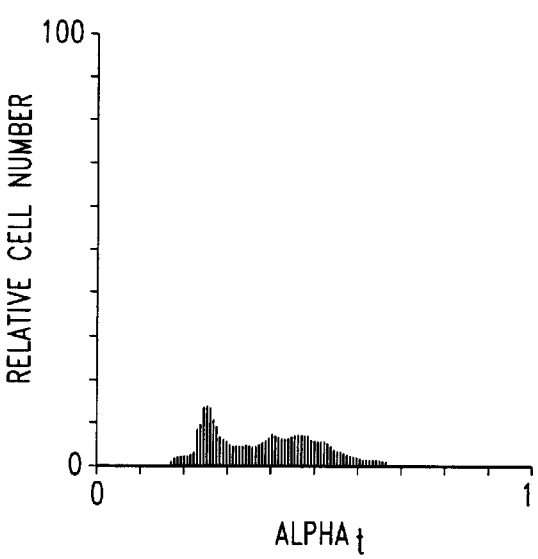
Figure 12:
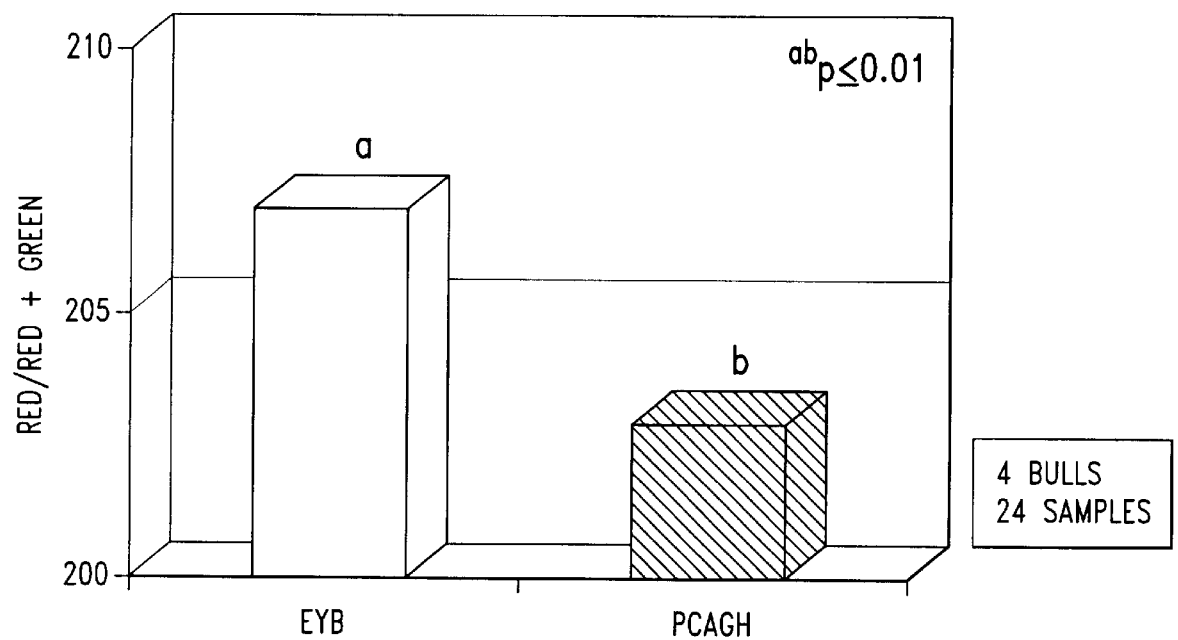
FIG. 12 is a chart illustrating the susceptibility of sperm DNA after thawing to acid or heat denaturation for sperm frozen in egg yolk buffer (EYB) or PCAGH extender.
Figure 13:
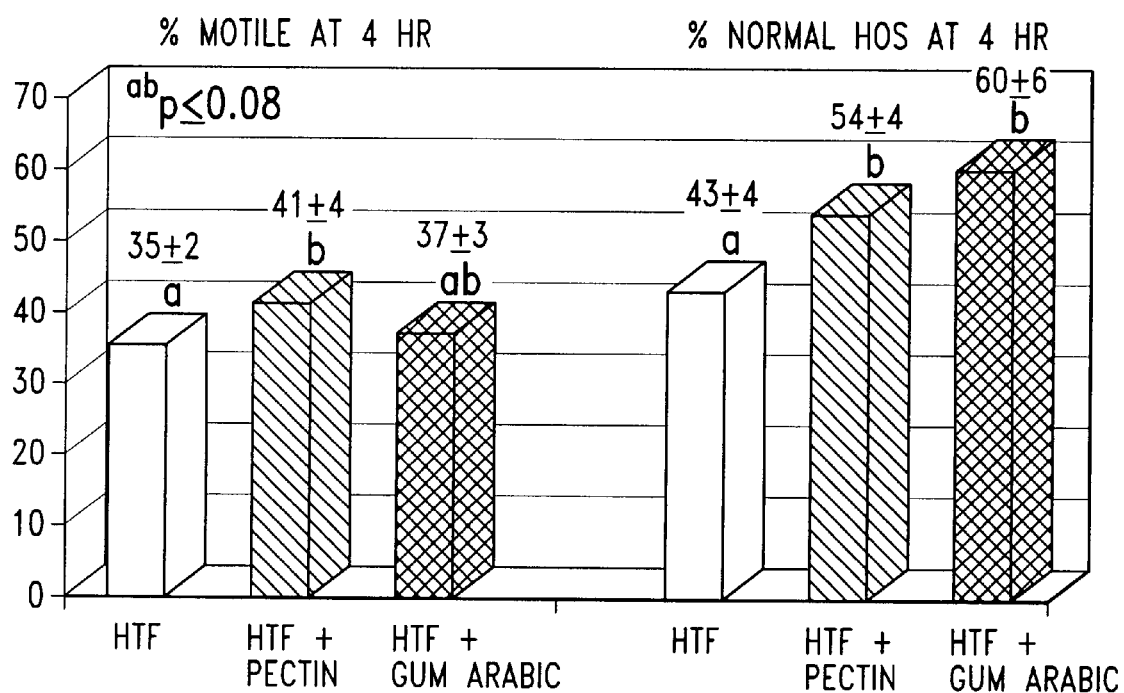
FIG. 13 is a graph showing the percentage of human sperm which are motile or have normal membranes after 4 hours culture in HTF media with or without PCAGH.
Figure 14:
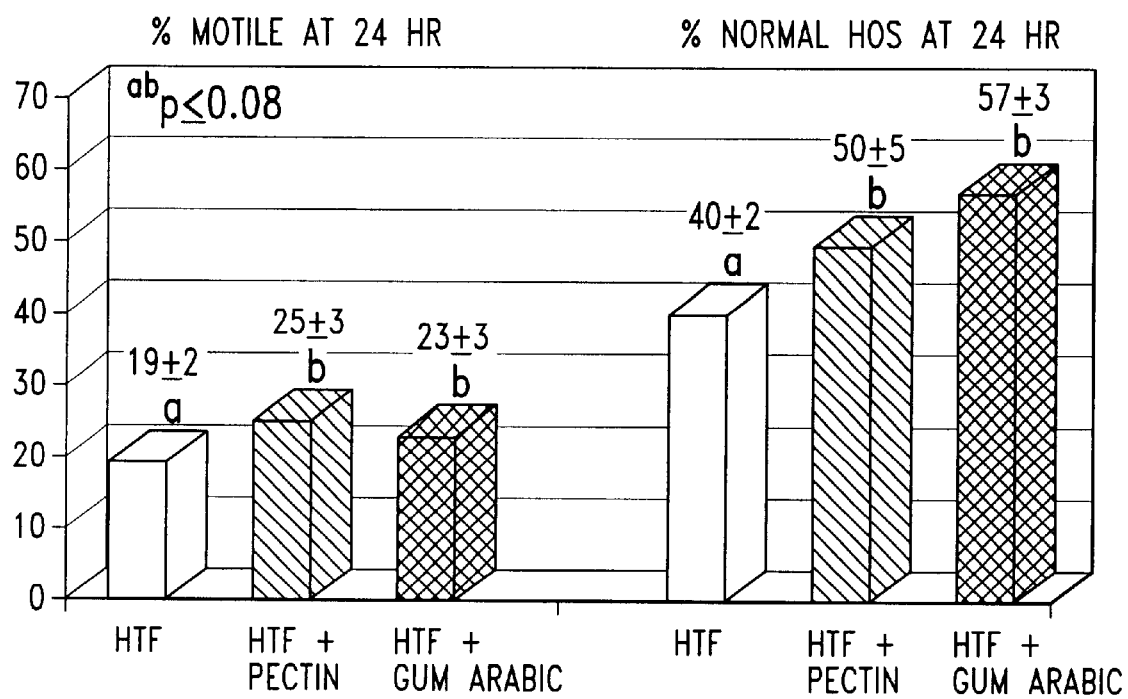
FIG. 14 is a chart showing the percentage of human sperm that are motile and have normal membranes after 24 hour culture in HTF media with or without a PCAGH.
Figure 15:
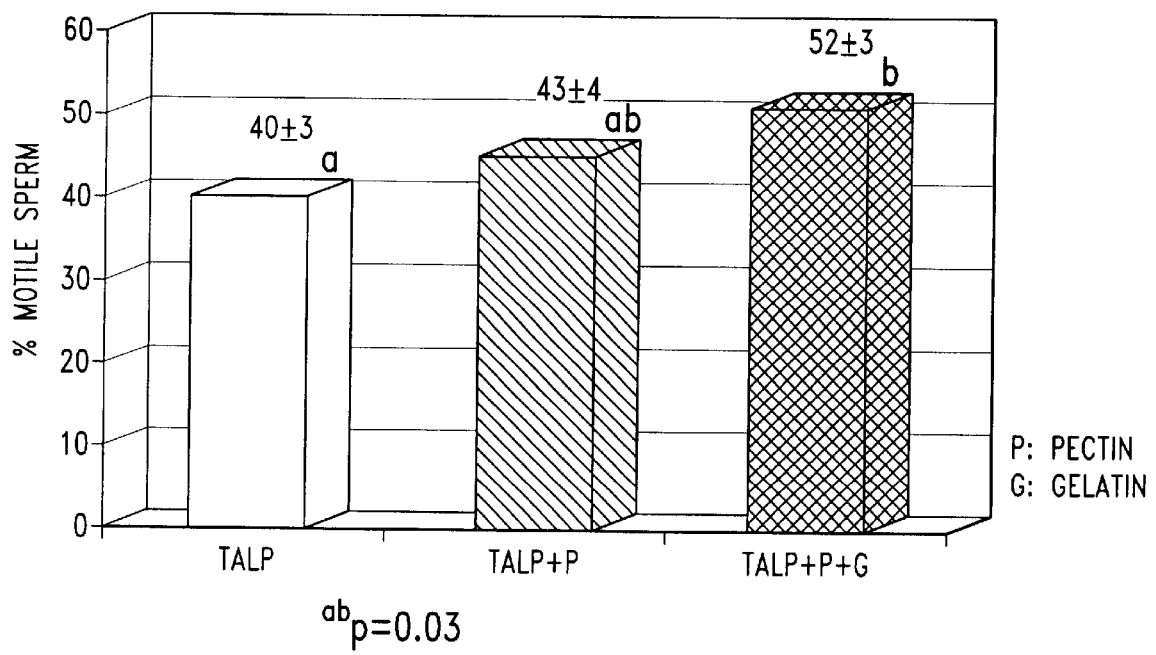
FIG. 15 is a chart presenting results of motility of sperm following a 5 hour culture in TALP with various additives.
Figure 16:
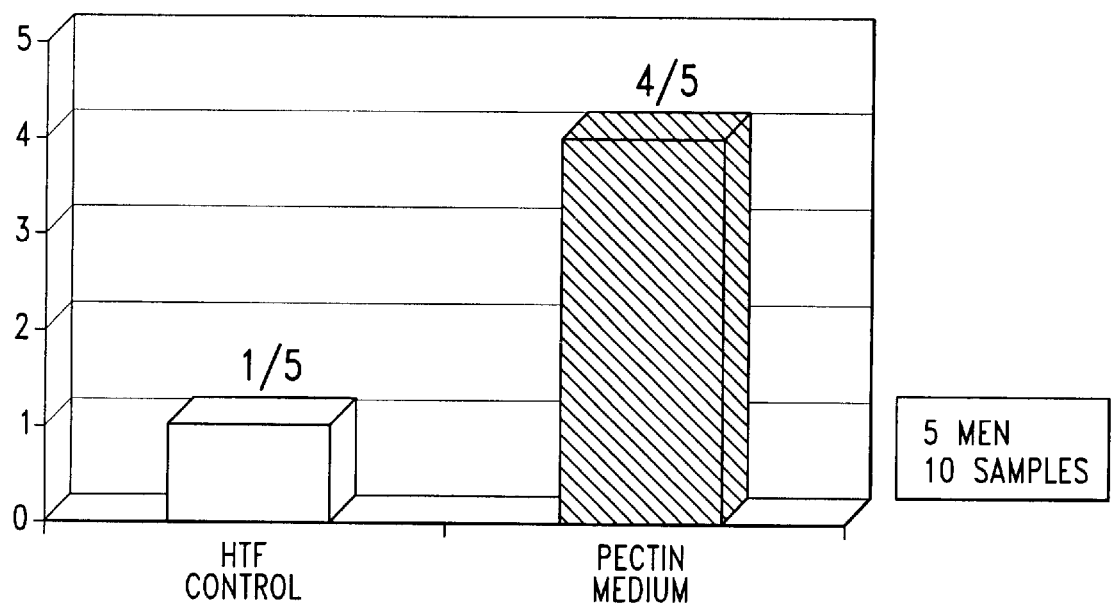
FIG. 16 is a chart showing the number of men who have >5% motile sperm after 72 hour culture in HTF medium with or without a PCAGH.

Human sperm frozen with a PCAGH, as compared to that frozen with standard Tris-egg yolk (TEY), show improved function. Bull sperm recovered after freezing and thawing in the PCAGH containing extender also have superior percent motility as compared to sperm frozen in a Tris-Egg yolk extender (FIG. 8), their survival over time in culture is better (FIG. 9), and they have less lipid membrane peroxidation and chromatin damage (FIGS. 10–12).

This extender also allows sperm to be frozen without utilizing milk products or egg products which may carry pathogens and which require special handling conditions prior to sperm freezing.

TABLE 8

NON-EGG YOLK CONTAINING SEMEN EXTENDER

| Ingredient | Percent |
|---|---|
| Sodium Citrate | 2.9 |
| Type IV Soy Lecithin | 1 |
| Bovine Serum Albumin | 2 |
| Pectin | 0.05 |
| Glycerol | 10 |

Example 7

Sperm Dilution (Extension) and Culture Technique

Sperm samples are obtained as described above (see Example 1). Basal medium is used throughout as follows: glucose-free TALP (Table 1) is prepared for separation of bovine sperm, TALP supplemented with glucose (5 mM glucose) is prepared for separation of other animal sperm, and human tubal fluid (HTF) is prepared for separation of human sperm. All supplies are purchased from Sigma, St. Louis, Mo., or Fertility Technologies, Natick, Mass. Sperm are separated from semen using a wash solution containing PCAGH or placed directly into media alone. Culture or extender medium is made by adding 5 mg/ml albumin, 0.5% gelatin or 0.1% PVA and an effective amount of PCAGH to basal medium. Specifically, PCAGH concentrations of 0.05% for pectin or gum arabic, 0.5% for arabic acid or arabinogalactan and 0.1% for gum guar or galacturonic acid are used.

Figure 17:
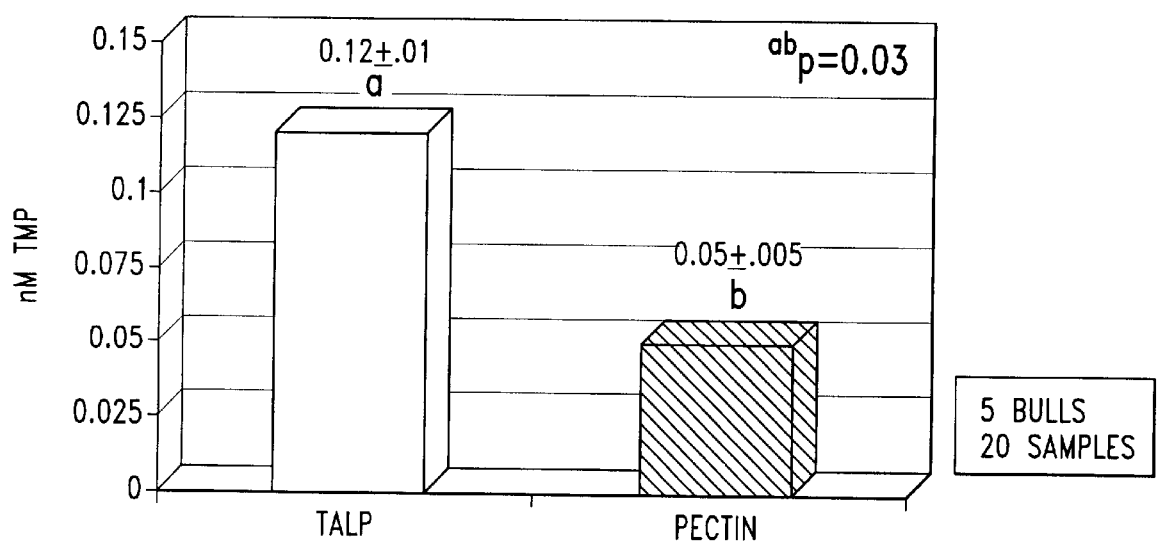
FIG. 17 shows the levels of lipid peroxidation of sperm cultured for 4 hours with or without a PCAGH.

Cultured sperm are incubated at 37° C.–39° C. in 5% CO$_2$ and humidified air. At 8-hour intervals the sperm survival rate is determined. Additionally, motility, viability and sperm penetration rates may be evaluated. Sperm cultured with 0.05% pectin or 0.05% gum arabic live longer and swim faster throughout the culture time period than sperm in control media with no PCAGH (FIGS. 13–16). They also have less lipid peroxidation and overall better membrane function (FIG. 17).

Figure 18:
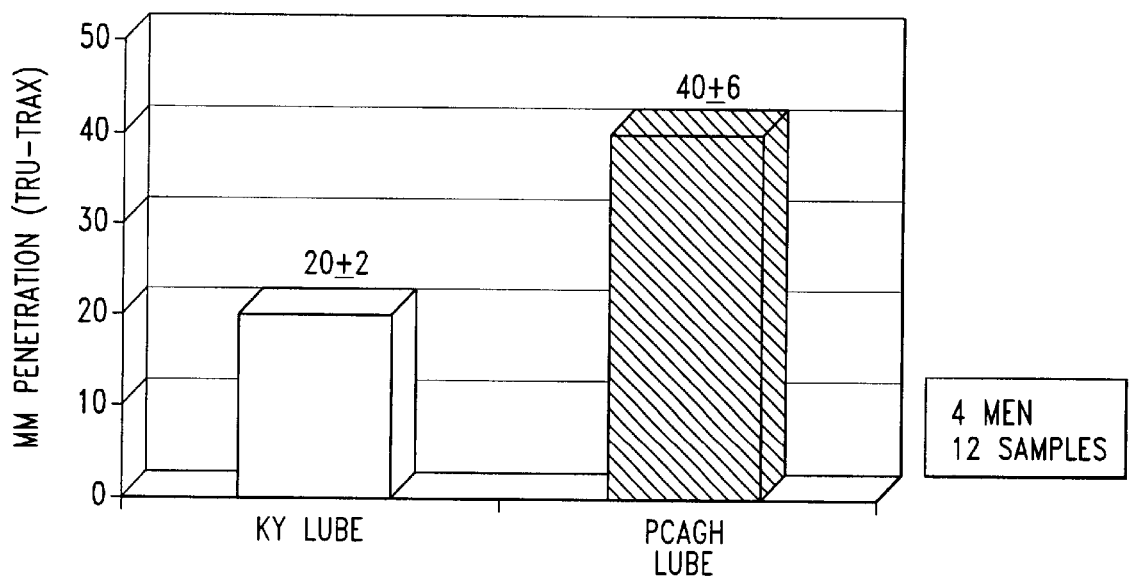
FIG. 18 is a graph illustrating penetration of bovine cervical mucus after 30 minutes incubation of raw semen with a PCAGH or KY lubricant.

Sperm for direct transfer into a female are diluted (extended) by adding a medium to a sperm sample and transferring the diluted sperm sample into the female via a catheter. In vitro testing of the efficacy of sperm extended in this manner to penetrate cervical mucus has shown that sperm in a PCAGH medium penetrate mucus faster than do those in control medium (Table 9; FIG. 18).

TABLE 9

MEAN BOVINE CERVICAL MUCUS PENETRATION IN MM AT 30 MINUTES OF INCUBATION IN EXTENDING MEDIUM

| control TALP | 20 mm |
|---|---|
| arabinogalactan-containing medium | 35 mm |
| pectin-containing medium | 40 mm |
| arabic acid-containing medium | 27 mm |
| gum arabic-containing medium | 22 mm |

Example 8

Lubricant Containing PCAGH

A base lubricant of 50% glycerine and 50% petroleum jelly is prepared. Alternately, a commercial non-toxic lubricant base such as Slippery Stuff (Wallace-Ofarrel, Puyallup, Wash.) or a mixture of polyethylene oxide, carboxypolymethylene and methylparaben is used. PCAGH is added at 0.5–1.0% for gum arabic or pectin or 5–10% for arabinogalactan. Sodium hydroxide is added to correct the pH to 7.4. In some embodiments, 0.5% polyvinyl alcohol or gelatin are added to improve sperm mucus penetration. For in vitro testing, semen samples are mixed with the PCAGH containing lube at 2 parts semen to 1 part lube. Sperm motility and viability are observed at 30 min intervals, and the mucus penetration test is done to evaluate sperm performance as compared to that seen for sperm in commercially available lubricants or in raw semen alone.

Figure 19:
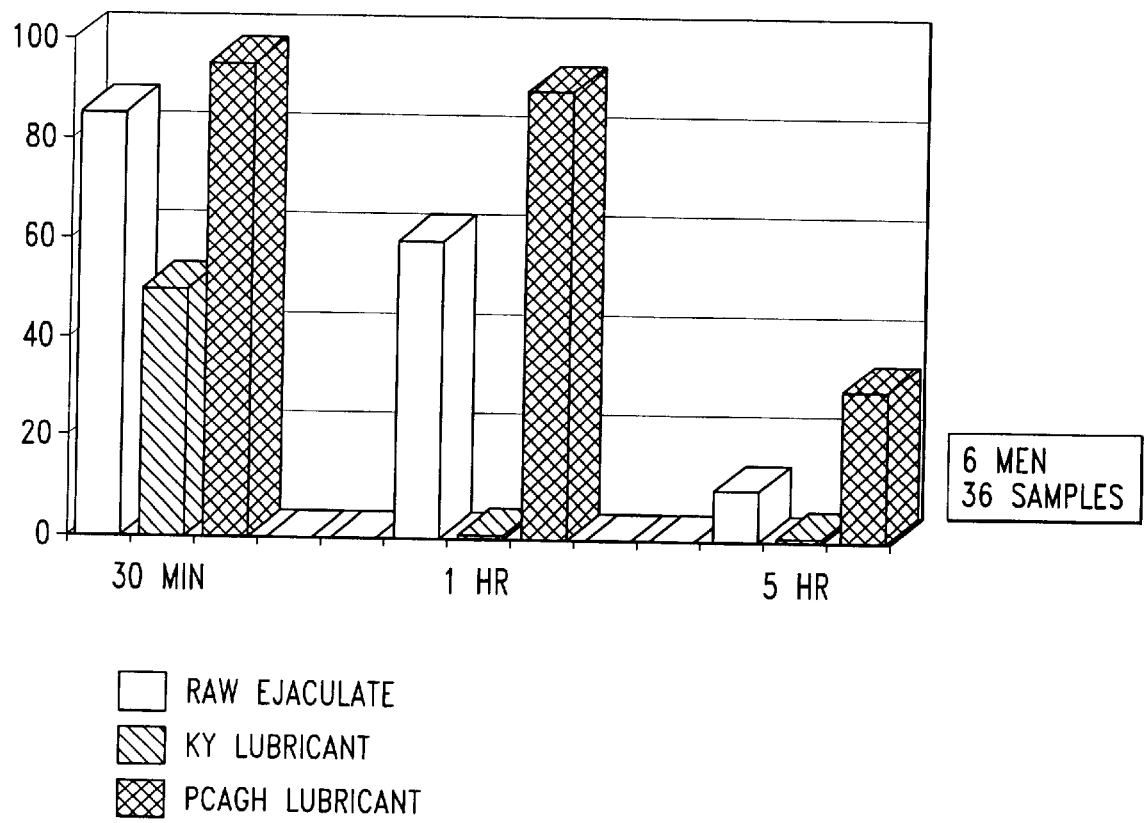
FIG. 19 is a graph illustrating the progressive motility of sperm over time when incubated in semen alone or in KY lubricant or a PCAGH lubricant.

Sperm show significantly better motility over time in the glycerin and petroleum jelly lubricant containing arabinogalactan or pectin than either KY jelly® or Priority Care (FIG. 19). KY lube has been reported to be spermicidal, but Priority Care is marketed as a "nonspermicidal" lubricant.

Sperm showed an increased ability to penetrate cervical mucus in lubricant containing 20% arabinogalactan or 1% pectin (Table 10) as well as increased penetration in a PCAGH lube compared to KY lube (FIG. 18).

TABLE 10

MEAN BOVINE CERVICAL MUCUS PENETRATION IN MM AT 30 MINTUTES OF INCUBATION FOR LUBE PRODUCT

| Priority Care | 8 mm |
|---|---|
| Arabinogalactan Containing Lube | 22 mm |
| Pectin Containing Lube | 17 mm |

Example 9

Testing of PCAGH on Vaginal Mucosa

A product containing sperm and PCAGH, such as either sperm freezing extender or lubricant, is tested for irritation of vaginal mucosa both in vitro and in vivo.

In vitro testing is conducted by incubating vaginal epithelial cell monolayers with solutions of product and evaluating (1) histological changes and (2) cell growth of vaginal epithelial cells (VEC). (1) Briefly, VEC are collected from macaque monkeys and cultured in DME: Ham's F12 (50:50) media containing 10% fetal bovine serum, growth factors (e.g., epidermal growth factor at 10 ng/ml) and antibiotics (1% antibiotic/antimycotic premix, Gibco). VEC are cultured in standard medium for 24 hours on Matrigel-coated (Collaborative Biochemical, Bedford, Vt.) coverslips placed in wells of 24-well tissue culture plates in order to optimize polarization, differentiation and secretory capacity. Cells are then cultured with low and high concentration (e.g., 0.005% to 30%, depending on the viscosity of the PCAGH) of solutions of product for 12, 24 and 48 hours. At the end of each incubation period, coverslips are rinsed with PBS and preserved in tissue fixative. Cells are stained with hematoxylin/eosin and observed histologically for signs of cellular degeneration. (2) VEC are plated at an intermediate density ($5 \times 10^3$ cells/well, 96-well tissue culture microplate) in standard culture medium. Following a 24-hour attachment period, cells are cultured in treatment (e.g., 0.005% to 30% product concentration) or control media for five days. Cell growth is determined at 24-hour intervals over the five-day treatment period using a modification of the MTT endpoint assay. In this assay system, growth is correlated to uptake of MTT by cell mitochondria and conversion to an insoluble blue formazan crystal which can be evaluated spectrophotometrically at 560 nm following solubilization in propanol (R. Mosmann, *J. Immunol. Methods* 65:55–63, 1983).

Example 10

Isolation of Oocytes, Embryos, and ESC

Sperm cells from a male donor are obtained either from a fresh ejaculate in raw semen or a refrigerated or frozen sample processed by washing or extending as described herein.

Oocytes from a female are obtained by aspiration of follicles during surgery, ultrasonic guided transvaginal aspiration, or aspiration of ovaries removed from the female. Oocytes may be obtained from fetal females, nonhormonally stimulated females (yielding immature primary oocytes), or hormonally stimulated females treated with follicle stimulating hormone or its equivalent (yielding mature, secondary oocytes).

Embryos may be obtained by in vitro fertilization (IVF) of oocytes and subsequent culture, flushing of the oviduct after fertilization and retrieval of embryos, flushing of the uterus after fertilization and retrieval of embryos, thawing of previously frozen embryos, or nuclear transfer and cloning of embryos. Cloned embryos are produced by fusing unfertilized oocytes with disaggregated cells of an existing embryo in order to produce multiple embryos, which are genetically identical.

Cloned embryos can also be obtained through the use of embryonic stem cells. Embryonic stem cells are ongoing cell lines of totipotent cells which came from an individual embryo. These cells are grown in a petri dish containing thousands of single cells, which, if fused with an inactive oocyte, can lead to the production of genetically similar animals.

Example 11

Oocyte Quality Assay

Oocyte quality is determined by the ability of the cumulus cells surrounding the oocyte to expand during incubation in M199 medium with or without 50 µg/ml luteinizing hormone for 22 hours. Normal oocytes will have >3–5 layers of expanded cumulus. Normal cumulus cell expansion is required for oocytes to perform normally in IVF.

Alternatively, oocyte quality is determined by staining the oocytes with a 1% aceto-orcein stain and determining the percentage of oocytes entering metaphase II.

This is a required maturational step which allows the oocyte to have only half of the chromosome number of the female.

Example 12

Embryonic Quality Assays

Embryonic development may be evaluated by a variety of tests including normal cleavage or division of the embryo in culture (Lindner and Wright, *Theriogenology* 20:407, 1983); normal formation of a blastocyst cavity at an appropriate time in culture; counting the number and health of cells found in the embryo using Hoechst 33342 stain (Pursel et al., *Theriogenology* 24:687); transfer to a female and establishment of a pregnancy; and transfer to a female and subsequent birth of a normal offspring.

Example 13

Oocyte and Embryo Freezing Techniques

Oocytes and embryos are added to a PCAGH containing medium consisting of phosphate buffered saline, and 0.05% pectin or gum arabic. Additionally, 18% Ficoll may be added. A final concentration of 40% ethylene glycol is obtained and oocytes are rapidly vitrified by placing them in liquid nitrogen vapor prior to plunging into liquid nitrogen. Alternately, oocytes or embryos in PCAGH media are added to 3.5 M DMSO or 1.5M propanediol and then packaged in freezing straws and placed in a programmable freezer or exposed to liquid nitrogen vapor for 1–2 hours. Frozen straws are then plunged into liquid nitrogen for storage. Oocytes or embryos are evaluated for normal development in culture, and after transfer as described in Examples 11 and 12.

Freezing in PCAGH containing media allows oocytes and embryos to be frozen without the use of serum which can carry pathogens and cause concern for international shipments or transfer into women. Embryos develop with better and more normal cell numbers in PCACH freeze medium and have better pregnancy rates after transfer.

Example 14

Oocyte and Embryo Culture Techniques

Oocytes and embryos are cultured in a balanced salt medium such as CZB or M199 containing 0.005–0.1% PCAGH and amino acids. Somatic cells and/or 50 µg/ml luteinizing hormone are optionally added. Oocyte quality is determined at about 24 hours. Embryo quality is evaluated at 24 hour intervals over a one week time period.

PCAGH medium allows more oocytes to reach metaphase II in culture, and more embryos to develop with higher cell numbers during culture. Also embryos transferred after culture result in a higher pregnancy rate than that seen with embryos cultured in standard media. The ability to replace serum in this culture media diminishes the oversized development seen in offspring resulting from IVF, thought to be due to growth factors in the serum.

It will be appreciated that, although specific embodiments of the invention have been described herein for purposes of illustration, various modifications may be made without departing from the spirit and scope of the invention. Accordingly, the invention is not limited except as by the appended claims.

We claim:

1. A method for improving the post-coitus function of sperm deposited intravaginally in a female animal during coitus, comprising placing a nonspermicidal lubricant in a vagina of an animal prior to coitus, wherein the animal subsequently has coitus and wherein the nonspermicidal lubricant comprises arabinogalactan and a nonspermicidal lubricious compound.

2. A method for improving the post-insemination function of sperm deposited intravaginally in a female animal by artificial insemination, comprising placing a nonspermicidal lubricant in a vagina of an animal prior to insemination, wherein the animal subsequently has artificial insemination and wherein the nonspermicidal lubricant comprises arabinogalactan and a nonspermicidal lubricious compound.

3. A method for improving post-ejaculatory sperm function, comprising applying a nonspermicidal lubricant to the interior of a sperm collection receptacle or to a medical device used in an assisted reproduction technique prior to deposition of sperm in the receptacle or device, wherein sperm is subsequently deposited in the receptacle or device and wherein the nonspermicidal lubricant comprises arabinogalactan and a nonspermicidal lubricious compound.

4. The method of claim 3 wherein the nonspermicidal lubricant is applied to the interior of a sperm collection receptacle.

5. The method of claim 3, wherein the nonspermicidal lubricant is applied to a medical device used in an assisted reproduction technique.

6. The method of any one of claims 1, 2, 3, 4 or 5 wherein the nonspermicidal lubricious compound comprises a carbomer.

* * * * *